(12) United States Patent
Lozier et al.

(10) Patent No.: US 10,179,017 B2
(45) Date of Patent: Jan. 15, 2019

(54) ORTHOPEDIC TOOL FOR BONE FIXATION

(71) Applicant: Zimmer, Inc., Warsaw, IN (US)

(72) Inventors: Antony J. Lozier, Warsaw, IN (US);
Daniel P. Murphy, Warsaw, IN (US);
Matthew Prygoski, Warsaw, IN (US);
Michael Giordano, Osceola, IN (US);
Donald L. Yakimicki, Warsaw, IN (US); Jeffrey Bassett, Jupiter, FL (US);
Michael Scott Collins, San Marcos, CA (US)

(73) Assignee: Zimmer, Inc., Warsaw, IN (US)

( * ) Notice: Subject to any disclaimer, the term of this patent is extended or adjusted under 35 U.S.C. 154(b) by 281 days.

(21) Appl. No.: 15/126,159

(22) PCT Filed: Apr. 3, 2015

(86) PCT No.: PCT/US2015/024263
§ 371 (c)(1),
(2) Date: Sep. 14, 2016

(87) PCT Pub. No.: WO2015/153981
PCT Pub. Date: Oct. 8, 2015

(65) Prior Publication Data
US 2017/0071649 A1 Mar. 16, 2017

Related U.S. Application Data

(60) Provisional application No. 61/974,554, filed on Apr. 3, 2014, provisional application No. 62/005,006, filed on May 30, 2014.

(51) Int. Cl.
*A61B 17/92* (2006.01)
*A61B 17/88* (2006.01)
*A61B 17/00* (2006.01)

(52) U.S. Cl.
CPC .............. *A61B 17/92* (2013.01); *A61B 17/88* (2013.01); *A61B 2017/00367* (2013.01);
(Continued)

(58) Field of Classification Search
CPC ...... A61B 17/068; A61B 17/92; A61B 17/162
See application file for complete search history.

(56) References Cited

U.S. PATENT DOCUMENTS 3,584,629 A 6/1971 Hoef et al.
3,618,842 A 11/1971 Bryan
(Continued)

FOREIGN PATENT DOCUMENTS

CN 86100996 A 9/1986
CN 2145361 Y 11/1993
(Continued)

OTHER PUBLICATIONS

"3M Staplizer Powered Metaphyse", [Online]. Retrieved from the Internet: <URL: http://www.wemed1.com/Products/spec.asp?ItemNumber=OR-3M-T100&Code=zzor3mc100>, (Accessed Apr. 22, 2013), 1 pg.
(Continued)

*Primary Examiner* — Andrew Yang
(74) *Attorney, Agent, or Firm* — Schwegman Lundberg & Woessner, P.A.

(57) ABSTRACT

A orthopedic tool (10) for bone fixation is provided for driving a bone pin into a fractured bone to stabilize the fractured bone by maintaining the fractured bone in a reduced state. The tool may be a handheld device including a magazine (56) having a plurality of passageways (98) containing one or more bone pins (62) positioned within the passageways. The tool may also include a pneumatically—powered piston (64) having a projection (70) that is sized for receipt within the plurality of passageways, the projection
(Continued)

applying sufficient force to the bone pin to drive the bone pin out of the magazine and into the fractured bone.

20 Claims, 7 Drawing Sheets

(52) U.S. Cl.
CPC ............... *A61B 2017/00548* (2013.01); *A61B 2017/00734* (2013.01); *A61B 2017/922* (2013.01)

(56) References Cited

U.S. PATENT DOCUMENTS

| | | | |
|---|---|---|---|
| 3,662,939 A | 5/1972 | Bryan | |
| 3,752,161 A | 8/1973 | Bent | |
| 3,815,476 A | 6/1974 | Green et al. | |
| 3,842,839 A | 10/1974 | Mails et al. | |
| 3,905,276 A | 9/1975 | Noiles et al. | |
| 4,298,074 A | 11/1981 | Mattchen | |
| 4,349,028 A | 9/1982 | Green | |
| 4,540,110 A | 9/1985 | Bent et al. | |
| 4,728,876 A | 3/1988 | Mongeon et al. | |
| 4,890,597 A | 1/1990 | Ekstrom | |
| 4,901,712 A | 2/1990 | Voegell et al. | |
| 4,909,419 A | 3/1990 | Yamada et al. | |
| 4,915,013 A | 4/1990 | Moraht et al. | |
| 4,938,408 A | 7/1990 | Bedi et al. | |
| 4,951,861 A | 8/1990 | Schulze et al. | |
| 5,049,775 A | 9/1991 | Smits | |
| 5,080,273 A | 1/1992 | Meyer | |
| 5,086,749 A | 2/1992 | Ekstrom | |
| 5,125,923 A | 6/1992 | Tanner et al. | |
| 5,136,469 A | 8/1992 | Carusillo et al. | |
| 5,149,603 A | 9/1992 | Fleming et al. | |
| 5,160,795 A | 11/1992 | Milliman | |
| 5,163,519 A | 11/1992 | Mead et al. | |
| 5,265,582 A | 11/1993 | Bhogal | |
| 5,282,861 A | 2/1994 | Kaplan | |
| 5,330,487 A | 7/1994 | Thornton et al. | |
| 5,363,834 A | 11/1994 | Stuchlik | |
| 5,366,459 A | 11/1994 | Yoon | |
| 5,370,037 A | 12/1994 | Bauer et al. | |
| 5,398,861 A | 3/1995 | Green | |
| 5,400,536 A | 3/1995 | Milliman | |
| 5,415,631 A | 5/1995 | Churinetz et al. | |
| 5,431,322 A | 7/1995 | Green et al. | |
| 5,485,887 A | 1/1996 | Mandanis | |
| 5,497,758 A | 3/1996 | Dobbins et al. | |
| 5,507,750 A | 4/1996 | Goble et al. | |
| 5,515,838 A | 5/1996 | Anderson | |
| 5,569,264 A | 10/1996 | Tamminmaki et al. | |
| 5,613,483 A | 3/1997 | Lukas et al. | |
| 5,628,444 A | 5/1997 | White | |
| 5,664,552 A | 9/1997 | Kunimoto | |
| 5,669,369 A | 9/1997 | Scott | |
| 5,687,897 A | 11/1997 | Fa et al. | |
| 5,704,150 A | 1/1998 | Milliman | |
| 5,709,334 A | 1/1998 | Sorrentino et al. | |
| 5,711,472 A | 1/1998 | Bryan | |
| 5,755,213 A | 5/1998 | Gardner, Jr. et al. | |
| 5,755,726 A | 5/1998 | Pratt et al. | |
| 5,769,781 A | 6/1998 | Chappuis | |
| 5,772,096 A | 6/1998 | Osuka et al. | |
| 5,775,312 A | 7/1998 | Wilkinson et al. | |
| 5,779,130 A | 7/1998 | Alesi et al. | |
| 5,782,821 A | 7/1998 | Couch | |
| 5,785,228 A | 7/1998 | Fa et al. | |
| 5,803,733 A | 9/1998 | Trott et al. | |
| 5,859,359 A | 1/1999 | Reid | |
| 5,862,972 A | 1/1999 | Green et al. | |
| 5,865,360 A | 2/1999 | White | |
| 5,878,734 A | 3/1999 | Johnson et al. | |
| 5,878,736 A | 3/1999 | Lotuaco, III | |
| 5,896,933 A | 4/1999 | White | |
| 5,902,306 A | 5/1999 | Norman | |
| 5,911,722 A | 6/1999 | Adler et al. | |
| 5,913,303 A | 6/1999 | Kotsiopoulos | |
| 5,918,791 A | 7/1999 | Sorrentino et al. | |
| 5,924,413 A | 7/1999 | Johnson et al. | |
| 5,954,259 A | 9/1999 | Viola et al. | |
| 5,954,689 A | 9/1999 | Poulsen | |
| 5,957,119 A | 9/1999 | Perry et al. | |
| 5,957,951 A | 9/1999 | Cazaux et al. | |
| 5,980,528 A | 11/1999 | Salys | |
| 5,989,214 A | 11/1999 | van de Wijdeven | |
| 5,997,500 A | 12/1999 | Cook et al. | |
| 6,006,704 A | 12/1999 | Phillips et al. | |
| 6,010,508 A | 1/2000 | Bradley | |
| 6,015,078 A | 1/2000 | Almeras et al. | |
| 6,016,945 A | 1/2000 | Phillips et al. | |
| 6,039,231 A | 3/2000 | White | |
| 6,042,571 A | 3/2000 | Hjertman et al. | |
| 6,059,749 A | 5/2000 | Marx | |
| 6,197,041 B1 | 3/2001 | Shichman et al. | |
| 6,223,658 B1 | 5/2001 | Rosa et al. | |
| 6,286,497 B1 | 9/2001 | Levkov | |
| 6,306,125 B1 | 10/2001 | Parker et al. | |
| 6,371,099 B1 | 4/2002 | Lee | |
| 6,371,348 B1 | 4/2002 | Canlas et al. | |
| 6,387,113 B1 | 5/2002 | Hawkins et al. | |
| 6,470,872 B1 | 10/2002 | Tiberius et al. | |
| 6,493,217 B1 | 12/2002 | Jenkins, Jr. | |
| 6,532,947 B1 | 3/2003 | Rosa et al. | |
| 6,578,565 B2 | 6/2003 | Casas Salva | |
| 6,613,011 B2 | 9/2003 | Castellano | |
| 6,620,135 B1 | 9/2003 | Weston et al. | |
| 6,766,795 B1 | 7/2004 | Sullivan | |
| 6,786,379 B2 | 9/2004 | Largo | |
| 6,851,447 B1 | 2/2005 | Carroll | |
| 6,877,647 B2 | 4/2005 | Green et al. | |
| 7,066,940 B2 | 6/2006 | Riedel et al. | |
| 7,069,922 B1 | 7/2006 | Orr | |
| 7,172,615 B2 | 2/2007 | Morriss et al. | |
| 7,237,545 B2 | 7/2007 | Masse | |
| 7,320,687 B2 | 1/2008 | Lee | |
| 7,427,283 B2 | 9/2008 | Roger | |
| 7,441,684 B2 | 10/2008 | Shelton, IV et al. | |
| 7,445,619 B2 | 11/2008 | Auge, II et al. | |
| 7,448,525 B2 | 11/2008 | Shelton, IV et al. | |
| 7,455,655 B2 | 11/2008 | Alexandre et al. | |
| 7,481,347 B2 | 1/2009 | Roy | |
| 7,665,396 B1 | 2/2010 | Tippmann, Jr. | |
| 7,765,999 B1 | 8/2010 | Stephens et al. | |
| 8,052,691 B2 | 11/2011 | Zwirnmann et al. | |
| 8,221,433 B2 | 7/2012 | Lozier | |
| 8,603,102 B2 | 12/2013 | Lozier et al. | |
| 8,852,202 B2 | 10/2014 | Lozier et al. | |
| 9,987,067 B2 | 6/2018 | Giordano et al. | |
| 2001/0044637 A1 | 11/2001 | Jacobs | |
| 2002/0077661 A1 | 6/2002 | Saadat | |
| 2002/0165549 A1 | 11/2002 | Owusu-Akyaw et al. | |
| 2002/0178901 A1 | 12/2002 | Bergstrom | |
| 2002/0188170 A1 | 12/2002 | Santamore et al. | |
| 2003/0074021 A1 | 4/2003 | Morriss et al. | |
| 2003/0195498 A1 | 10/2003 | Treat et al. | |
| 2003/0225411 A1 | 12/2003 | Miller | |
| 2004/0138683 A1 | 7/2004 | Shelton et al. | |
| 2004/0144012 A1 | 7/2004 | Adams | |
| 2004/0158196 A1 | 8/2004 | Garitano et al. | |
| 2004/0189258 A1 | 9/2004 | Lehmann et al. | |
| 2005/0010168 A1 | 1/2005 | Kendall | |
| 2005/0096661 A1 | 5/2005 | Farrow et al. | |
| 2005/0119694 A1 | 6/2005 | Jacobs et al. | |
| 2005/0131414 A1 | 6/2005 | Chana | |
| 2005/0159752 A1 | 7/2005 | Walker et al. | |
| 2005/0165394 A1 | 7/2005 | Boyce et al. | |
| 2005/0188973 A1 | 9/2005 | Monks | |
| 2005/0188977 A1 | 9/2005 | Wygant | |
| 2005/0283189 A1 | 12/2005 | Rosenblatt | |
| 2006/0124118 A1 | 6/2006 | Dobbins | |
| 2006/0217729 A1 | 9/2006 | Eskridge et al. | |
| 2006/0241589 A1 | 10/2006 | Heim et al. | |
| 2006/0293648 A1 | 12/2006 | Herzon | |

(56) References Cited

U.S. PATENT DOCUMENTS

| | | |
|---|---|---|
| 2007/0017497 A1 | 1/2007 | Masse |
| 2007/0021779 A1 | 1/2007 | Garvin et al. |
| 2007/0156175 A1 | 7/2007 | Weadock et al. |
| 2007/0169765 A1 | 7/2007 | Forster et al. |
| 2007/0175465 A1 | 8/2007 | Quinn et al. |
| 2007/0233133 A1 | 10/2007 | Cohen et al. |
| 2007/0235014 A1 | 10/2007 | Tiberius et al. |
| 2007/0270784 A1 | 11/2007 | Smith et al. |
| 2008/0015630 A1 | 1/2008 | Rousso |
| 2008/0029573 A1 | 2/2008 | Shelton et al. |
| 2008/0058820 A1 | 3/2008 | Harp |
| 2008/0058867 A1 | 3/2008 | Dean |
| 2008/0103355 A1 | 5/2008 | Boyden et al. |
| 2008/0125784 A1 | 5/2008 | Rabiner et al. |
| 2008/0135598 A1 | 6/2008 | Burke et al. |
| 2008/0208251 A1 | 8/2008 | Weadock et al. |
| 2008/0221580 A1 | 9/2008 | Miller et al. |
| 2008/0228104 A1 | 9/2008 | Uber et al. |
| 2008/0251569 A1 | 10/2008 | Smith et al. |
| 2008/0255607 A1 | 10/2008 | Zamlok |
| 2008/0269754 A1 | 10/2008 | Lutz et al. |
| 2008/0272172 A1 | 11/2008 | Zemlok et al. |
| 2008/0281343 A1 | 11/2008 | Dewey et al. |
| 2008/0281353 A1 | 11/2008 | Aranyi et al. |
| 2008/0283570 A1 | 11/2008 | Boyden et al. |
| 2008/0283574 A1 | 11/2008 | Boyden et al. |
| 2008/0283577 A1 | 11/2008 | Boyden et al. |
| 2008/0294024 A1 | 11/2008 | Cosentino et al. |
| 2008/0296346 A1 | 12/2008 | Shelton, IV et al. |
| 2009/0018548 A1 | 1/2009 | Charles |
| 2009/0032003 A1 | 2/2009 | Masse |
| 2009/0032568 A1 | 2/2009 | Viola et al. |
| 2009/0050671 A1 | 2/2009 | Racenet et al. |
| 2009/0082715 A1 | 3/2009 | Charles |
| 2009/0090763 A1 | 4/2009 | Zemlok et al. |
| 2009/0108048 A1 | 4/2009 | Zemlok et al. |
| 2009/0108049 A1 | 4/2009 | Roy |
| 2009/0112243 A1 | 4/2009 | Boyden et al. |
| 2009/0118734 A1 | 5/2009 | Bhatnagar et al. |
| 2009/0118738 A1 | 5/2009 | Gerondale |
| 2009/0131937 A1 | 5/2009 | Medoff |
| 2009/0163943 A1 | 6/2009 | Cavanaugh et al. |
| 2009/0171354 A1 | 7/2009 | Deville et al. |
| 2009/0206136 A1 | 8/2009 | Moore et al. |
| 2009/0209990 A1 | 8/2009 | Yates et al. |
| 2009/0235910 A1 | 9/2009 | Maeda |
| 2009/0240245 A1 | 9/2009 | Deville et al. |
| 2009/0241931 A1 | 10/2009 | Masse |
| 2009/0259220 A1 | 10/2009 | Appling et al. |
| 2009/0264893 A1 | 10/2009 | Beale et al. |
| 2009/0264940 A1 | 10/2009 | Beale et al. |
| 2009/0270834 A1 | 10/2009 | Nisato et al. |
| 2009/0299359 A1 | 12/2009 | Swain |
| 2010/0012698 A1 | 1/2010 | Liang et al. |
| 2010/0024791 A1 | 2/2010 | Romney |
| 2010/0030205 A1 | 2/2010 | Herzon |
| 2010/0036391 A1 | 2/2010 | Zaleski et al. |
| 2010/0069943 A1 | 3/2010 | Roe |
| 2010/0076455 A1 | 3/2010 | Birkenbach et al. |
| 2010/0121355 A1 | 5/2010 | Gittings et al. |
| 2010/0126486 A1 | 5/2010 | Halmone et al. |
| 2010/0154767 A1 | 6/2010 | Masse |
| 2010/0305624 A1 | 12/2010 | Lozier et al. |
| 2012/0172885 A1 | 7/2012 | Drapeau et al. |
| 2012/0232556 A1 | 9/2012 | Mani et al. |
| 2012/0253411 A1 | 10/2012 | Lozier et al. |
| 2012/0274253 A1 | 11/2012 | Fair et al. |
| 2013/0204264 A1 | 8/2013 | Mani et al. |
| 2014/0074127 A1 | 3/2014 | Giordano et al. |
| 2014/0094863 A1 | 4/2014 | Lozier et al. |
| 2014/0318823 A1 | 10/2014 | Pedicini |
| 2015/0150617 A1 | 6/2015 | Giordano et al. |
| 2015/0201918 A1 | 7/2015 | Kumar et al. |
| 2016/0074088 A1 | 3/2016 | Mirza et al. |
| 2016/0199199 A1 | 7/2016 | Pedicini |

FOREIGN PATENT DOCUMENTS

| | | |
|---|---|---|
| CN | 2153482 Y | 1/1994 |
| CN | 102448389 A | 5/2012 |
| CN | 103596730 A | 2/2014 |
| CN | 102448389 B | 10/2014 |
| CN | 106456225 A | 2/2017 |
| EP | 0171967 A2 | 2/1986 |
| EP | 0171967 A3 | 2/1986 |
| EP | 1859749 A2 | 11/2007 |
| EP | 2452631 A1 | 5/2012 |
| JP | 2017510356 A | 4/2017 |
| WO | WO-9522934 A1 | 8/1995 |
| WO | WO-0162160 A1 | 8/2001 |
| WO | WO-2008018865 A1 | 2/2008 |
| WO | WO-2010138538 A1 | 12/2010 |
| WO | WO-2014011841 A1 | 1/2014 |
| WO | WO-2015153981 A2 | 10/2015 |
| WO | WO-2015153981 A3 | 10/2015 |

OTHER PUBLICATIONS

"U.S. Appl. No. 12/787,518, Notice of Allowance dated Apr. 26, 2012", 12 pgs.

"U.S. Appl. No. 12/787,518, Response filed Jan. 30, 2012 to Restriction Requirement dated Jan. 3, 2012", 2 pgs.

"U.S. Appl. No. 12/787,518, Restriction Requirement dated Jan. 3, 2012", 6 pgs.

"U.S. Appl. No. 13/493,200, Notice of Allowance dated Aug. 7, 2013", 11 pgs.

"U.S. Appl. No. 13/493,200, Response filed Jul. 3, 2013 to Restriction Requirement dated Jun. 5, 2013", 6 pgs.

"U.S. Appl. No. 13/493,200, Restriction Requirement dated Jun. 5, 2013", 8 pgs.

"U.S. Appl. No. 14/016,377, Non Final Office Action dated Feb. 17, 2016", 10 pgs.

"U.S. Appl. No. 14/098,877, Notice of Allowance dated Jun. 4, 2014", 9 pgs.

"U.S. Appl. No. 14/098,877, Preliminary Amendment filed Jan. 23, 2014", 7 pgs.

"U.S. Appl. No. 14/098,877, Response filed May 19, 2014 to Restriction Requirement dated Apr. 17, 2014", 8 pgs.

"U.S. Appl. No. 14/098,877, Restriction Requirement dated Apr. 17, 2014", 8 pgs.

"U.S. Appl. No. 14/413,761, Supplemental Preliminary Amendment filed May 21, 2015", 6 pgs.

"Chinese Serial No. 201080022735.4, Office Action dated Nov. 20, 2013", (W/ English Translation), 18 pgs.

"Chinese Application Serial No. 201080022735.4, Response filed Apr. 4, 2014 to Office Action dated Nov. 20, 2013", (W/ English Translation), 14 pgs.

"European Application Serial No. 10727219.7, Examination Notification Art. 94(3) dated Apr. 2, 2015", 4 pgs.

"European Application Serial No. 10727219.7, Office Action dated Feb. 3, 2012", 2 pgs.

"European Application Serial No. 10727219.7, Office Action dated Mar. 26, 2012", 1 pg.

"European Application Serial No. 10727219.7, Response filed Aug. 10, 2012 to Office Action dated Feb. 3, 2012", 12 pgs.

"International Application Serial No. PCT/US2010/036126, International Preliminary Report on Patentability dated Dec. 8, 2011", 6 pgs.

"International Application Serial No. PCT/US2010/036126, International Search Report and Written Opinion dated Sep. 13, 2010", 10 pgs.

"International Application Serial No. PCT/US2013/050024, International Preliminary Report on Patentability dated Jan. 22, 2015", 7 pgs.

"International Application Serial No. PCT/US2013/050024, International Search Report dated Sep. 4, 2013", 3 pgs.

"International Application Serial No. PCT/US2013/050024, Written Opinion dated Sep. 4, 2013", 5 pgs.

(56) References Cited

OTHER PUBLICATIONS

"International Application Serial No. PCT/US2015/024263, International Search Report dated Oct. 9, 2015", 6 pgs.

"International Application Serial No. PCT/US2015/024263, Written Opinion dated Oct. 9, 2015", 6 pgs.

"Polysorb™ Meniscal Stapler XLS Device", [Online]. Retrieved from the Internet: <URL: http://www.sportssurgery.com/sportsmedicine/pageBuilder.aspx?topicID=31604>, (2008), 1 pg.

"Repairing Fractured Bones by Use of Bioabsorbable Composites", Langley Research Center, Tech Briefs, [Online]. Retrieved from the Internet: <http://www.techbriefs.com/component/content/5/5?task=view>., (Sep. 2, 2006), 2 pgs.

"The Staple (Biomet's Meniscal Stapler CO2 Gun)", [Online]. Retrieved from the Internet: <URL: http://www.biomet.com/sportsmedicine/getFile.cfm?id=1055&rt=inline>, (1999), 2 pgs.

"U.S. Appl. No. 14/413,761, Examiner Interview Summary dated Feb. 6, 2018", 3 pgs.

"U.S. Appl. No. 14/413,761, Non Final Office Action dated Oct. 2, 2017", 10 pgs.

"U.S. Appl. No. 14/413,761, Response filed Feb. 2, 2018 to Non Final Office Action dated Oct. 2, 2017", 12 pgs.

"European Application Serial No. 16192264.6, Partial European Search Report dated Aug. 23, 2017", 18 pgs.

"International Application Serial No. PCT/US2015/024263, International Preliminary Report on Patentability dated Oct. 13, 2016", 8 pgs.

U.S. Appl. No. 14/413,761, filed Jan. 9, 2015, Bone Fixation Tool.

U.S. Appl. No. 14/016,377, filed Sep. 3, 2013, Soft Tissue Connector.

U.S. Appl. No. 12/787,518, filed May 26, 2010, Bone Fixation Tool, U.S. Pat. No. 8,221,433.

U.S. Appl. No. 13/493,200, filed Jun. 11, 2012, Bone Fixation Tool, U.S. Pat. No. 8,603,102.

U.S. Appl. No. 14/098,877, filed Dec. 6, 2013, Bone Fixation Tool, U.S. Pat. No. 8,852,202.

"Chinese Application Serial No. 201580026459.1, Office Action dated May 31, 2018", w/ English Translation, 8 pgs.

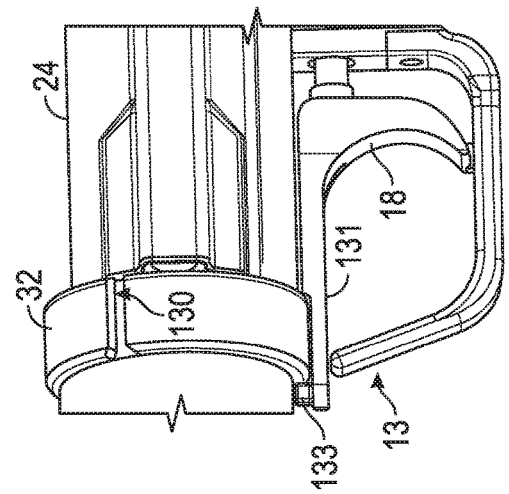
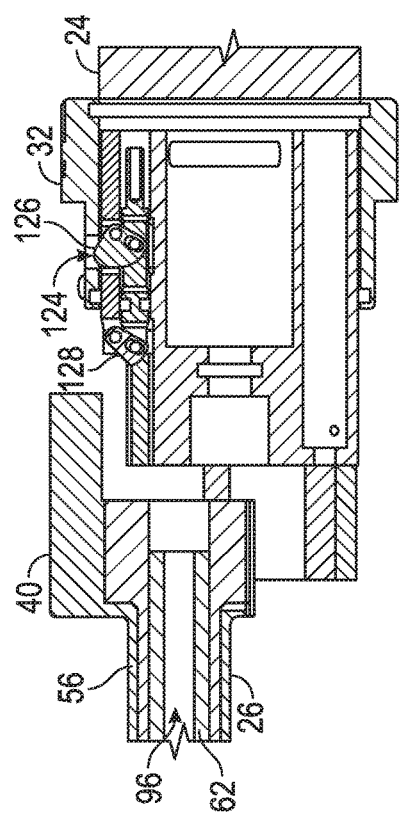
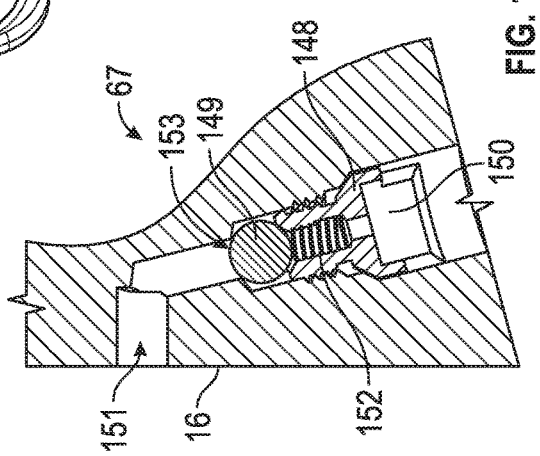
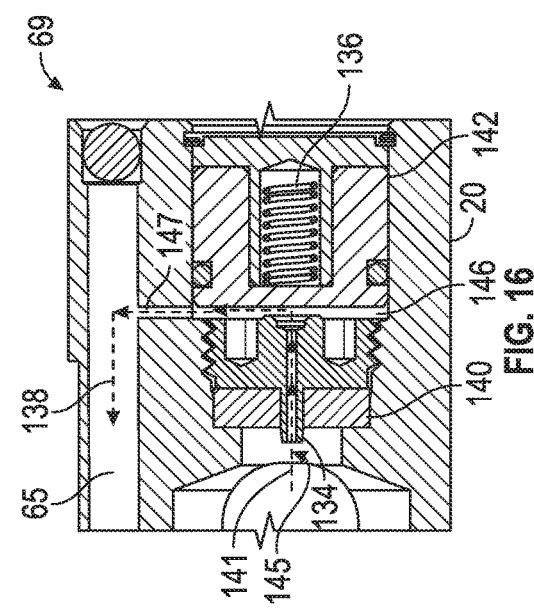
FIG. 15
FIG. 14
FIG. 16
FIG. 17

ORTHOPEDIC TOOL FOR BONE FIXATION

CLAIM OF PRIORITY

This application is a U.S. National Stage Filing under 35 U.S.C. 371 from International Application No. PCT/US/2015/024263, filed on 3 Apr. 2015, and published as WO 2015/0153981 A2 on 8 Oct. 2015, claims the benefit of U.S. Provisional Patent Application Ser. No. 61/974,554, filed on Apr. 3, 2014 and U.S. Provisional Patent Application Ser. No. 62/005,006, filed on May 30, 2014, the benefit of priority of which are claimed hereby, and which are incorporated by reference herein in their entirety.

TECHNICAL FIELD

The present disclosure relates to orthopedic tools for bone fixation, and more particularly, to orthopedic tools and methods for driving a bone pin into a fractured bone to stabilize a fractured bone.

BACKGROUND

In trauma cases involving bone fracture, such as peri-articular and comminuted (multi-part) fractures, the bone fracture can produce multiple bone fragments. In operation, these fragments can be reduced and temporarily secured together prior to more permanently fixing the bone fragments together. It is important for bone fragments to be closely reassembled for proper healing to occur. Conventionally, temporary fixation can be accomplished using various external fixation devices, such as clamps, and internal fixation devices such as pins and wires. As the bone fragments are put back together, temporary fixation can be achieved.

External fixation devices, such as clamps, are bulky and may require invasive surgical procedures. Also, internal fixation devices can be difficult to drive into the bone fragments and can extend externally from the bone fragments interferring with external plating for permanent fixation. For example, pilot holes can be drilled in the bones and a metal wire can be passed through the pilot holes. The wires hold the bones in place while the surgeon reassembles the fractured bone elements. Wire installation can be difficult and is not a trivial task. In some examples, wires can include a trocar tip that is used to drill through the bone and in such cases no pilot is needed. However, it can be a laborious task to slowly drill and guide the wires through the bone.

Permanent fixation for healing can be achieved with the use of bone plates and screws. For example, bone plate can be placed on the exterior of the bones and screws are inserted through the plate and into the bone to hold the pieces together. For the temporary fixation provided by the wires to be effective, they are typically located closely to where the plates and screws need to be located. As such, there is a significant amount of pre-planning required for precise wire placement that will not interfere with the permanent means of fixation, For example, wires can be bent, removed, and repositioned so that the plates can be applied effectively. Removal of the wires requires the reattachment of the installation tool which requires that the wires be unbent and straightened. The process of bending, re-bending, and un-bending the wires can be inconvenient and is also a waste of precious operating room time. Many aspects of using wires as temporary fixation in conventional methods adds to the total time spent in the surgery, from arduous drilling and challenging placement to difficult removal.

OVERVIEW

The present disclosure relates generally to orthopedic tools for bone fixation such as a bone pin gun. A bone pin gun can also be referred to generally as a "rapid fixation tool" or "tool." These guns or tools, and their related aspects and methods of use, can be used to facilitate driving one or more bone pins into bone when stabilizing a bone fracture.

The present disclosure relates to a gas-powered bone pin gun that can drive a bone pin into a fractured bone to stabilize the fractured bone by maintaining the fractured bone in a reduced state. In certain examples, the bone pin may be used to temporarily stabilize the fractured bone prior to incorporating permanent fixation devices. The bone pin gun can be a handheld device including a magazine having a plurality of passageways, where the plurality of passageways can be configured to receive the bone pin. The bone pin gun can include a gas-powered piston having a projection that is sized for receipt within the passageways of the magazine. As discussed herein, the projection can be configured to apply sufficient force to the bone pin to drive the bone pin out of the magazine and into the fractured bone. Such fixation technology can be applicable to methods, devices, systems used in, for example, orthopedic and dental procedures.

The present inventors have recognized, among other things, that a problem to be solved can include the inconvenience and disadvantages of using clamps and wires for temporarily stabilizing bone fragments in a bone fracture. As discussed above, the external fixation devices can be bulky and can require invasive, time consuming surgical procedures and the internal fixation devices can be difficult and time consuming to implant into the bone. Further, some internal fixation devices can extend externally from the bone fragments and interfere with external plating for permanent fixation. The present subject matter can help provide a solution to this problem, such as by providing an efficient tool for applying the temporary fixation devices that can reduce the surgical time without hindering the installation of permanent fixation devices, As discussed herein, the bone pin gun can be gas-powered. The safety features and usability of the bone pin gun become increasingly important to protect the patient, surgeon, and others in the operating room while using the bone pin gun. For example, the alignment of the bone pin relative to a patient's anatomy can be important. With handheld delivery tools, alignment is completely dependent on the surgeon. Accidentally firing the bone pin gun prior to proper alignment can be extremely hazardous, even life-threatening.

The present disclosure provides a bone pin gun including various safety and usability features. For example, the bone pin gun of the present disclosure can have one or more modes such as a ready mode, an assemble mode, and a depth mode. As discussed herein, each mode enables a user to perform a function of the bone pin gun, while preventing other functions from being performed such that a user is prevented from accidentally firing the bone pin gun while attempting to perform other functions such adjust the length of the bone pin or assemble the bone pin gun. Further, the bone pin gun has a gas valve and a filter valve that can seal off a gas inlet and a gas outlet when the bone pin gun is not in use to minimize or prevent contamination from entering the bone pin gun, which would potentially be introduced to the patient.

The bone pin gun of the present disclosure further provides for automatic advancement of the magazine including the bone pins such that the time spent between firing bone pins can be minimized. Thus, the bone pin gun of the present disclosure can allow for very rapid stabilization. This can be important, for example, in severe trauma cases where an orthopedic surgeon has a short time window to reduce fractured bones before other surgeons must step in for life-saving procedures The bone pin gun of the present disclosure can also automatically trim the bone pin with a single break. The single break can be advantageous in that is can minimize the production of bone pin fragments that can interfere with the functioning of the bone pin gun, enter a wound of the patient, or contaminate other medical equipment in the operating room. As discussed herein, the bone pin gun can include a trimming tip that can automatically trim the bone pin once the bone pin has been driven from the magazine and implanted into the patient.

To further illustrate the various examples disclosed herein, a non-list of examples is provided here:

In Example 1, a tool comprises a body portion including a barrel, a handle, and a mode selector ring, the mode selector ring rotatable about the barrel and configured to switch between a ready mode position and an assemble mode position; a magazine having a magazine head, a magazine nose extending from the magazine head, and a plurality of passageways, wherein one or more passageways of the plurality of passageways is configured to receive a bone pin; a magazine holder configured to receive the magazine; a collar defining an opening configured to receive a portion of the magazine holder; a piston having a head, a shaft extending from the head, and a projection coupled to the shaft, the projection configured to be received within a first passageway of the plurality of passageways; and a trigger coupled to the body portion, wherein, when the trigger is activated, the piston is configured to apply sufficient force to the bone pin to drive the bone pin axially from the first passageway.

In Example 2, the tool of Example 1 can be optionally configured such that when the mode selector ring is at the assemble mode position, the magazine holder is configured to be releasably coupled to the body portion and when the mode selector ring is at the ready mode position, the trigger is configured to be activated.

In Example 3, the tool of any one or any combination of Examples 1 or 2 can be optionally configured such that when the mode selector ring is at the ready mode position, the magazine holder is locked to the body portion.

In Example 4, the tool of any one or any combination of Examples 1-3 can be optionally configured such that when the mode selector ring is at the assemble mode position, the trigger is locked at an initial.

In Example 5, the tool any one or any combination of Examples 1-4 can be optionally configured such that the mode selector ring further includes a depth mode position such that the mode selector is rotatable about the barrel to switch between the depth mode position, the ready mode position, and the assemble mode position.

In Example 6, the tool of Example 5 can be optionally configured to include a depth selector positioned along the barrel, wherein, when the mode selector ring is at the depth mode position, the depth selector is configured to move along a length of the barrel to adjust a length of the bone pin that is driven axially from the first passageway.

In Example 7, the tool of Example 6 can be optionally configured such that when the mode selector ring is at the depth mode position, the trigger is locked at an initial position and the magazine holder is locked to the body portion, wherein, when the mode selector ring is at the ready mode position, the depth selector is locked in position along the barrel and the magazine holder is locked to the body portion, and wherein, when the mode selector ring is at the assemble mode position, the depth selector is locked in position along the barrel and the trigger locked at the initial position.

In Example 8, the tool of any one or any combination of Examples 1-7 can be optionally configured to include a pressurized gas source for supplying a pneumatic force to the head of the piston to axially translate the piston relative to at least the body portion and the magazine.

In Example 9, a tool comprises a body portion including a barrel, a handle, and a mode selector ring, the mode selector ring rotatable about the barrel and configured to switch between a ready mode position and an assemble mode position; a magazine having a magazine head, a magazine nose extending from the magazine head, and a plurality of passageways, wherein one or more passageways of the plurality of passageways is configured to receive a bone pin; a magazine holder configured to receive the magazine; a collar defining an opening configured to receive a portion of the magazine holder; a piston having a head, a shaft extending from the head, and a projection coupled to the shaft, the projection configured to apply sufficient force to the bone pin, when present within a first passageway of the plurality of passageways, to drive the bone pin from the first passageway; and an advancement pawl disposed within the body portion, the advancement pawl including a pawl shaft and a pawl head, wherein the pawl head is configured to interact with the magazine head to rotate the magazine and align a second passageway of the plurality of passageways with the projection.

In Example 10, the tool of Example 9 can be optionally configured such that the magazine head includes a plurality of fins, each fin of the plurality of fins having an angled surface relative to a longitudinal axis of the magazine, wherein the angled surface is configured to interact with the pawl head to rotate the magazine.

In Example 11, the tool of Example 10 can be optionally configured such that a first portion of the plurality of fins are arranged in a proximal row circumferentially spaced around the magazine head and a second portion of the plurality of fins are arranged in a distal row circumferentially spaced around the magazine head, the first portion of the plurality of fins circumferentially offset from the second portion of plurality of fins.

In Example 12, the tool of Example 10 can be optionally configured such that the pawl head has a shape including at least two angled surfaces relative to a longitudinal axis of the advancement pawl, the at least two angled surfaces of the pawl head configured to engage with one or more angled surfaces of the plurality of fins to rotate the magazine.

In Example 13, the tool of any one or any combination of Examples 9-12 can be optionally configured to include a trigger coupled to the body portion, wherein, when the trigger is activated, the piston is configured to drive the first bone pin axially from the first passageway.

In Example 14, the tool of any one or any combination of Examples 9-13 can be optionally configured such that the trigger has an initial position, an end position, and an intermediate position located between the initial position and end position, wherein, upon activation of the trigger from the initial position to the intermediate position, the piston is configured to drive the bone pin axially from the first passageway, and upon activation of the trigger from the intermediate position to the end position, the pawl head is configured to interact with the magazine head to rotate the magazine and align the second passageway with the projection.

In Example 15, the tool of any one or any combination of Examples 9-14 can be optionally configured such that the magazine holder includes a trimming end defining a trimming bore that is configured to align with the projection of the piston and trim the bone pin when the magazine rotates within the magazine holder.

In Example 16, the tool of Example 15 can be optionally configured such that the trimming bore includes a breaking edge including a curved surface and a relief edge having a chamfered surface including two straight surfaces forming an edge.

In Example 17, the tool any one or any combination of Examples 9-16 can be optionally configured such that a pressurized gas source for supplying a pneumatic force to the head of the piston to axially translate the piston relative to body portion and the magazine.

In Example 18, a system comprises a body portion including a barrel, a handle, and a mode selector ring, the mode selector ring rotatable about the barrel and configured to switch between a ready mode position and an assemble mode position; a magazine including a plurality of passageways, wherein one or more passageways of the plurality of passageways is configured to receive a bone pin; a magazine holder configured to receive the magazine; a collar defining an opening configured to receive a portion of the magazine holder; and a piston having a head, a shaft extending from the head, and a projection coupled to the shaft, the projection sized for receipt within a first passageway of the plurality of passageways, the projection configured to apply sufficient force to the bone pin when present within the first passageway, to drive the bone pin axially from the first passageway.

In Example 19, the system of Example 18 can be optionally configured to include at least one of: a plurality of magazines, wherein each magazine include at least one bone pin positioned in a first passageway of the plurality of passageways, one or more gas canisters for supplying a pneumatic force to the head of the piston to axially translate the piston relative to at least the body portion and the magazine.

In Example 20, the system of any one or any combination of Examples 18-19 can be optionally configured to include a trigger coupled to the body portion, wherein, when the trigger is activated, the piston is configured to drive the first bone pin axially from the first passageway; and an advancement pawl disposed within the body portion, the advancement pawl including a pawl shaft and a pawl head, wherein the pawl head is configured to interact with a magazine head to rotate the magazine and align a second passageway of the plurality of passageways with the projection.

In Example 21, the tool or system of any one or any combination of Examples 1-20 can optionally be configured such that all elements, operations, or other options recited are available to use or select from.

Each of these non-limiting examples can stand on its own, or can be combined in various permutations or combinations with one or more of the other examples.

These and other examples and features of the present orthopedic tool will be set forth in part in the following Detail Description. This Overview is intended to provide an overview of the present subject matter it is not intended to provide an exclusive or exhaustive explanation. The Detailed Description is included to provide further information about the present orthopedic tool.

BRIEF DESCRIPTION OF DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

FIG. 14 illustrates a cross-sectional view of a portion of the barrel and a portion of the magazine holder, in accordance with at least one example.

FIG. 15 illustrates a perspective view of a trigger assembly and the mode selector ring, in accordance with at least one example.

FIG. 16 illustrates a cross-sectional view of the gas valve as shown in FIG. 3, in accordance with at least one example.

FIG. 17 illustrates a cross-sectional view of the filter valve assembly, as shown in FIG. 3, in accordance with at least one example.

DETAILED DESCRIPTION

Example tools and methods for bone fixation for reducing and securing together bone fragments, which may serve as a temporary solution prior to more permanent fixation of the bone fragments, are described herein. For example, the present disclosure can provide a bone pin gun that can be used to deliver a bone pin into the bone fragments to secure the bone fragments together. The bone pin can remain in the patient's body over time, or the bone pin may absorb into the patient's body.

Figure 1:
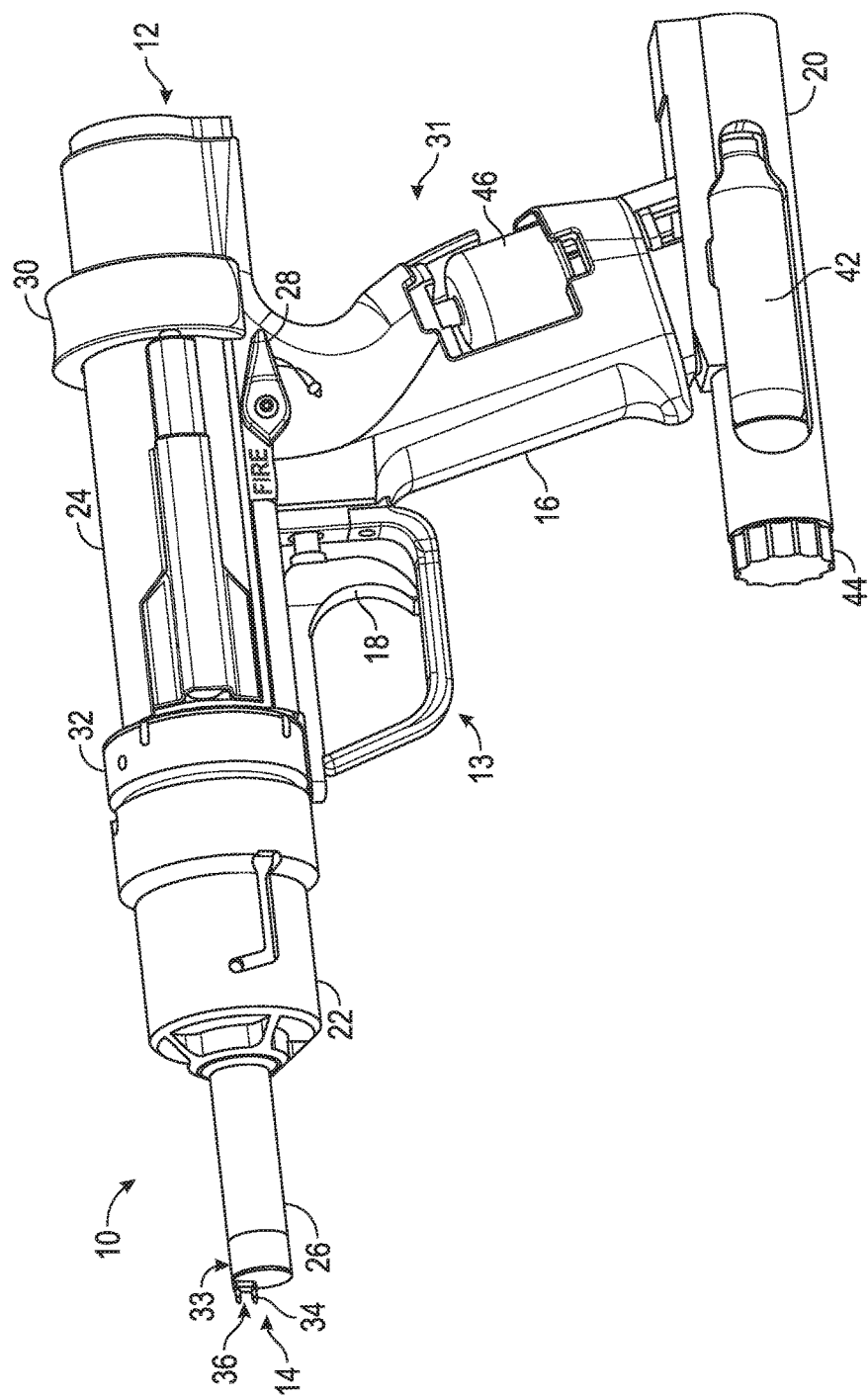
FIG. 1 illustrates a perspective view of a bone pin gun, in accordance with at least one example.
Figure 3:
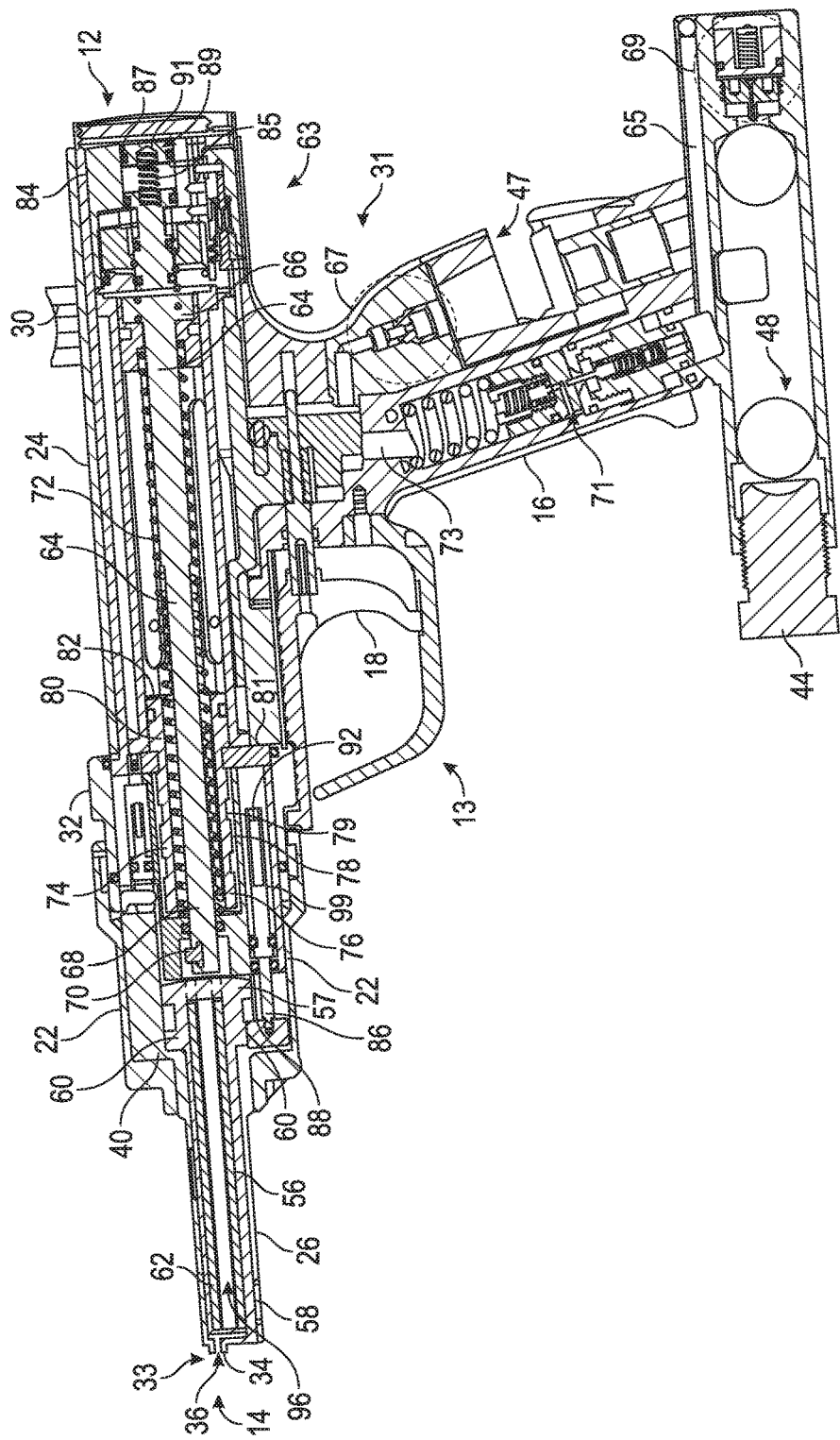
FIG. 3 illustrates a cross-sectional view of the bone pin gun, in accordance with at least one example.

FIG. 1 illustrates a perspective view of a bone pin gun 10, in accordance with at least one example. The bone pin gun 10 can be used for stabilizing a fracture bone, for example, by delivering a bone pin into the bone fragment. The bone pin gun 10 can extend from a proximal end 12 to a distal end 14, The bone pin gun 10 can include a body portion 31 having a barrel 24 and a handle 16, a magazine holder 26, a collar 22, and a trigger assembly 13 including a trigger 18. The bone pin gun 10 in FIG. 1 is shown as assembled and the collar 22 and the magazine holder 26 are coupled to the body portion 31. As discussed herein, the magazine holder 26 and collar 22 can be releasable coupled to the body portion 31, The magazine holder 26 can be configured to receive a magazine 56 (as shown in FIGS. 3 and 14) including one or more bone pins. The one or more bone pins can be driven from the magazine and into a bone fragment. In an example, the magazine holder 26 and/or the magazine can be disposable. Disengaging the collar 22 and the magazine holder 26 including the magazine from the body portion 31 can enable a user to replace the the magazine nose 26 and/or the magazine and bone pins.

As shown in FIG. 1, the bone pin gun 10 can include a gas housing 20 that can house a pressurized gas source such as gas canister 42. In an example, the body potion 31 can include a filter 46 housed within the handle 16. The gas housing 20 can receive and contain the gas canister 42 within the gas housing 20 via a screw top 44 that engages with the gas housing 20.

Figure 10:
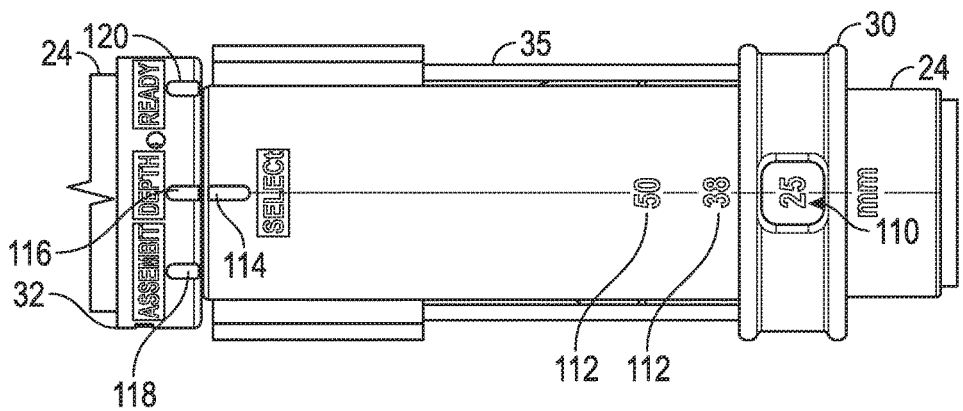
FIG. 10 illustrates a top view of a portion a barrel and a mode selector ring, in accordance with at least one example.

The body portion 31 can further include a mode selector ring 32 that can be rotatable about the barrel 24. The mode selector ring 32 can be configured to switch between at least two mode positions. In an example, the mode selector ring 32 can be configured to switch between three mode positions. For example, the mode selector ring 32 can be configured to switch between a ready mode position 120, an assemble mode position 118, and a depth selector position 116, as shown in FIG. 10.

The body portion 31 can also include a depth selector ring 30 positioned along the barrel 24. As discussed herein, when the mode selector ring 32 is at the depth mode position, the depth selector ring 30 can be configured to move along a length of the barrel 24 to adjust a length of the bone pin that is driven axially from the bone pin gun 10. Along with other safety features discussed herein, the bone pin gun 10 can include a safety 28 to minimize the risk of the bone pin gun 10 discharging unintentionally.

In an example, the magazine holder 26 can include a trimming end 33 defining a trimming bore 36 and a bone contacting surface 34. As discussed herein, the trimming end 33 can trim a bone pin that has been driven from the bone pin gun 10 and implanted into a patient with a single break.

The bone pin gun 10 can include a trigger assembly 13 including a trigger 18. As discussed herein, when the trigger 18 is activated (e.g. pressed), a pneumatic force can be applied to a piston 64 (shown in FIG. 3) within the barrel 24 to axially translate the piston 64 relative to at least the body portion 31 to drive a bone pin from the bone pin gun 10.

Figure 2:
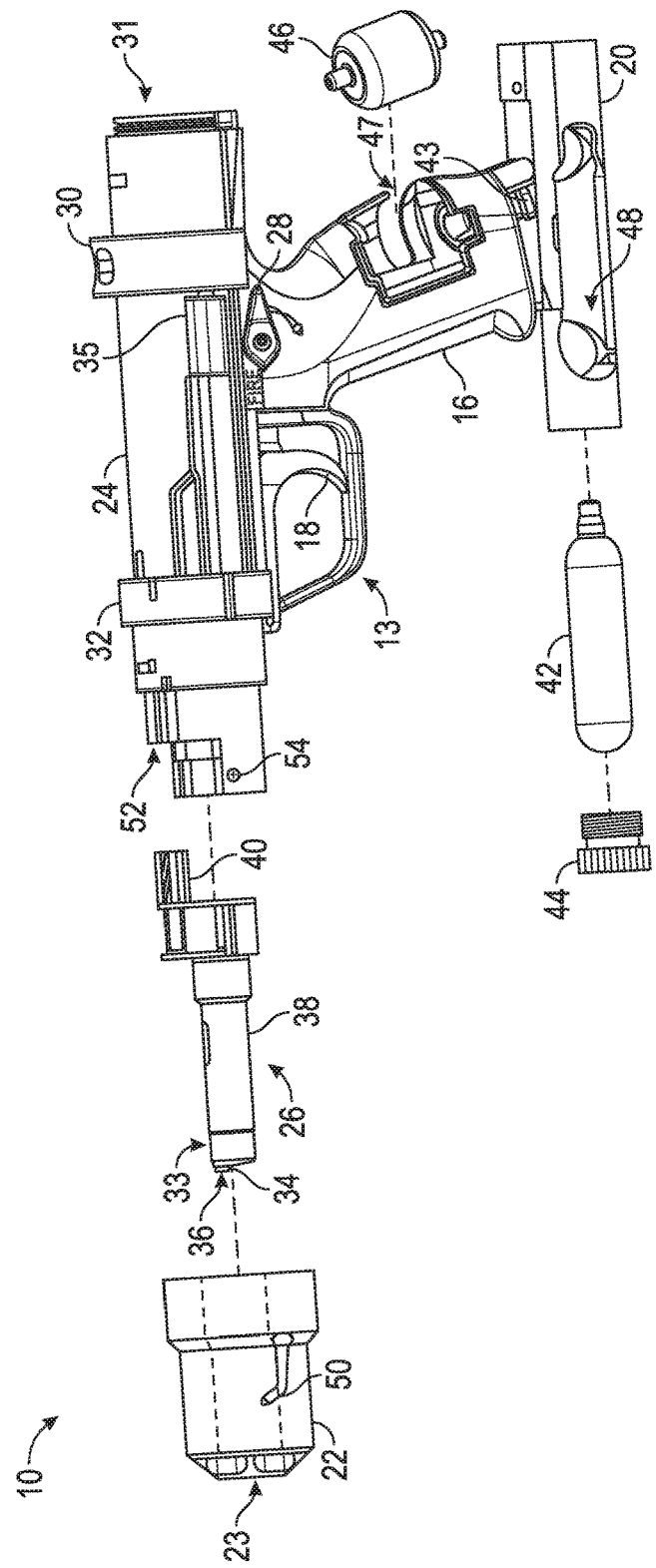
FIG. 2 illustrates an expanded perspective view of the bone pin gun as shown in FIG. 1, in accordance with at least one example.

FIG. 2 illustrates an expanded perspective view of the bone pin gun 10 as shown in FIG. 1, in accordance with at least one example. As discussed herein, the magazine holder 26 and the collar 22 can be configured to be releasably coupled to the body portion 31. For example, the barrel 24 can include an engaging end 52 that can be releasably coupled with the magazine holder 26 and collar 22.

The magazine holder 26 can include a magazine nose 38 and an engaging end 40. The magazine nose 40 can include the trimming end 33 that defines the trimming bore 36. The collar 22 can define an opening 23 that is configured to receive a portion of the magazine holder 26. For example, a portion of the magazine nose 38 can extend through the opening 23, The collar 22 and the magazine holder 26 can combine to form a unit that is releasably coupled to the body portion 31. In an example, the engaging end 40 of the magazine holder 26 can engage with a portion of the engaging end 52 of the barrel 24. For example, the engaging end 52 of the barrel 24 can include a projection 54 that interacts with a slot 50 formed in a sidewall of the collar 22. The slot 50 and the projection 54 can interact to couple the magazine holder 26 and the collar 22 to the body portion 31.

Figure 13:
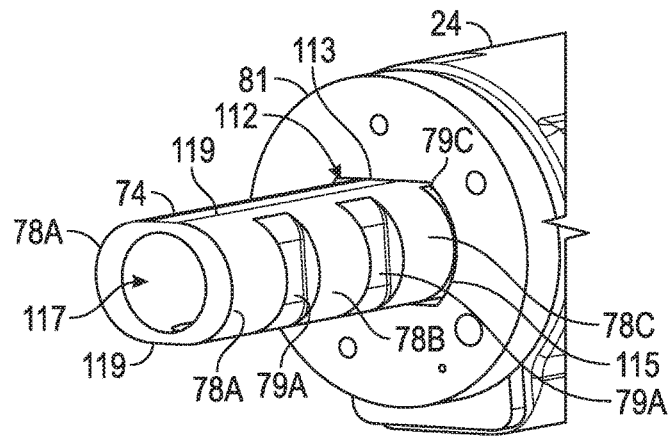
FIG. 13 illustrates an assembled view of the depth lock and the hard stop, in accordance with at least one example.

The bone pin gun 10 can include one or more rods 35 that are coupled to the depth selector ring 30 as well as a hard stop 74 (shown in FIGS. 3 and 13). As discussed herein, the depth selector ring 30 can move along the barrel 24 to adjust the position of the hard stop 74 within the barrel 24, which determines the length of the bone pin that is driven from the bone pin gun 10, The handle 16 can define an opening 47 in a side wall that can be configured to receive the filter 46. For example, the filer 46 can be received within the opening 47 and snapped into place within the handle 16, The filter 46 can be disposable and can be replaced as necessary. To replace the filter 46, tab 43 can be depressed to disengage the filter 46 from the handle 16 and the filter 46 can be replaced with an unused filter. As illustrated in FIG. 2, the gas housing 20 can define a bore 48 that is configured to receive the gas canister 42.

FIG. 3 illustrates a cross-sectional view of the bone pin gun 10, in accordance with at least one example. The bone pin gun 10 in FIG. 3 is shown as assembled, but does not include the gas canister 42 or the filter 46 (as shown in FIGS. 1 and 2). The bone pin gun 10 can include a magazine 56 having a magazine head 60 and a magazine nose 58. The magazine head 60 can include a. plurality of fins 57 that, as discussed herein, are configured to interact with an advancement pawl 86 to rotate the magazine 56 within the magazine holder 26 once a bone pin 62 has been discharged from the bone pin gun 10.

In an example, the magazine 56 can define a plurality of passageways 98 and a cannula 96. The plurality of passageways 98 and the cannula 96 can extend along a length of the magazine 56. One or more of the plurality of passageways 98 can be configured to receive a bone pin 62. As illustrated in FIG. 3, the magazine 56 can be positioned within the magazine holder 26 and a portion of the magazine holder 26 can be positioned through the collar 22. The magazine holder 26, including the magazine 56, and the collar 22 can be releasably coupled to the barrel 24. As discussed herein, the magazine holder 26 and collar 22 can be releasably coupled to the body portion 31 when the bone pin gun in an assemble mode.

In an example, the bone pin gun 10 can include a piston 64. piston 64 can fit into and translate axially within the barrel 24. The piston 64 can include a head 66, a shaft 68 extending from the head 66, and a projection 70 that is radially offset from the shaft 68. When assembled, the projection 70 can be aligned with one of the plurality of passageways 98 of the magazine 56. The projection 70 can be sized for receipt within the aligned passageway 98 to drive the bone pin 62 from the aligned passageway 98.

As shown in FIG. 3, the piston 64 is at a retracted position. For example, the piston 64 can be biased toward the retracted position such that the piston head 66 is positioned toward the proximal end 12 of the bone pin gun 10. A resilient member 72 can be positioned between the head 66 and a distal end of the barrel 24 to bias the piston head 66 toward the proximal end 12 of the bone pin gun 10. For example, the resilient member 72 can be configured to be in an uncompressed state when the piston 64 is at the retracted position, as shown in FIG. 3. In operation, as the piston 64 is forced down the barrel 24, the resilient member 72 can become compressed and can be configured to be in a compressed state as the head 66 moves toward the distal end 14 of the bone pin gun 10. As the piston 64 is forced down the barrel 24, the shaft 68 can extend within the cannula 96 of the magazine 56 and the projection 70 can extend within the passageway 98 aligned with the projection 70. When the projection 70 of the shaft 68 is received within the passageway 98, the projection 70 can apply sufficient force to the bone pin 62 to drive the bone pin 62 axially from the passageway 98 and into the fractured bone. After the bone pin 62 is driven from the bone pin gun 10, the resilient member 72 can be configured to transition from the compressed state to the uncompressed state and return the piston 64 to the retracted position toward the proximal end 12 of the bone pin gun 10.

As shown in FIG. 3, the bone pin gun 10 can include an advancement pawl 86 that is disposed within the body portion 31. The advancement pawl 86 can include a pawl shaft 99 and a pawl head 88. As discussed herein, the pawl head 88 can interact with the magazine head 60 to rotate the magazine 56 after a desired length of the bone pin 62 has been discharged from the bone pin gun 10.

The magazine holder 26 can include the trimming end 33 that defines a trimming bore 36. Once the bone pin 62 is discharged from the bone pin gun 10, the interaction between the advancement pawl 86 and the magazine 56 puts a portion of the bone pin 62 (e.g., the portion positioned within the trimming bore 36) in tension with the trimming bore 36 to trim e.g., break) the bone pin 62 along a desired location with a single break.

The bone pin gun 10 can include the depth selector ring 30 that is coupled to a hard stop 74 positioned within the barrel 24. The depth selector ring 30 can move along a length of the barrel 24 to change the position of the had stop 74 within the barrel 24 and adjust the length of the bone pin 62 discharged from the bon pin gun 10. As discussed herein, the depth selector ring 30 can be configured to move along a length of the barrel 24 when the bone pin gun 10 is in the depth mode.

In an example, the depth selector ring 30 can be coupled to the hard stop 74 via rods 35 (as shown in FIG. 2) such that moving the depth selector ring 30 along the barrel 24 moves the hard stop 74 within the barrel 24. in an example, moving the hard stop 74 within the barrel 24 can adjust the position of a stopping surface 82, of the hard stop 74, as shown in FIGS. 3 and 13. In an example, the stopping surface 82 can determine how far the piston 64 can translate axially with respect to the barrel 24 and therefore the position of the stopping surface limits how much of the piston 64 is received within the magazine 56. How much of the piston 64 that is received within the magazine 56 can determine the length of the bone pin 62 that is driven from the bone pin gun 10. Thus, the depth selector ring 30 can be configured to move along a length of the barrel 24 to adjust the amount (e.g., length) of the bone pins 62 that are driven from the bone pin gun 10 and into the bone fracture.

The bone pin gun 10 can be powered pneumatically, hydraulically, electrically (e.g., with batteries), and/or electromagnetically. In an example, when the trigger 18 is pulled (e.g., activated), compressed air can be released and force the piston 64 and the projection 70 coupled thereto forward along the barrel 24 until the projection 70 projects beyond the barrel 24 and within the passageway 98 of the magazine 56 aligned with the projection 70.

As shown in FIG. 3, the body portion 31 of the gas housing 20 can include a gas valve assembly 69 and the handle 16 can include a filter valve assembly 67, As discussed herein, the gas valve assembly 69 and the filter valve assembly 67 can seal a gas inlet 145 (as shown in FIG. 16) and a gas outlet 150 (as shown in FIG. 17) of the bone pin gun 10 to prevent contaminants from entering the interior of the bone pin gun 10.

In an example, the bone pin gun 10 can include a regulator 71 and a valve assembly 63. As discussed herein, the regulator 71 can be provided to control the pressure of the gas that is delivered to valve assembly 63. The bone pin gun 10 can include a trigger 18 coupled to the body portion 31. When the trigger 18 is pulled, the pressurized gas from the valve assembly 63 can be released.

As discussed herein, when the trigger 18 is initially activated from an initial position to an intermediate position, the pressurized gas can be released from the valve assembly 63 and drive the piston 64 down the barrel 24 to discharge a bone pin 62 from the bone pin gun 10. However, once the trigger 18 is activated past the intermediate position (e.g., to an end position), a portion of the pressurized gas can interact with the advancement pawl 86 to rotate the magazine 56. The slight delay between when the pressurized gas reaches the piston 64 versus when the pressurized gas reaches the advancement pawl 86, can ensure that the desired length of the bone pin 62 has been discharged and that the piston 64 is not positioned within the magazine 56 before the magazine 56 is rotated and the bone pin 62 is trimmed.

Figure 4A:
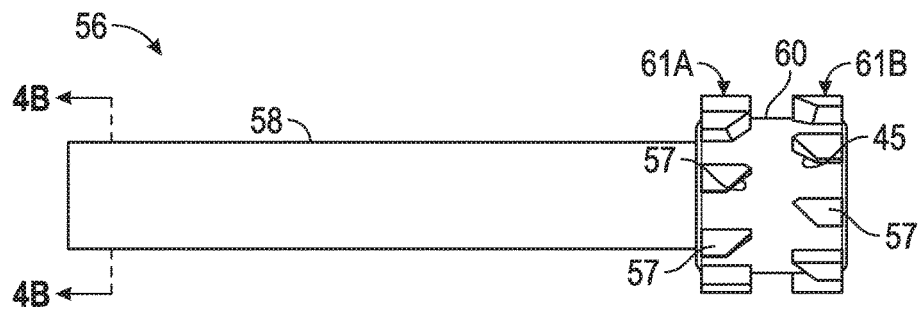
FIG. 4A illustrates a side view of a magazine, in accordance with at least one example.
Figure 4B:
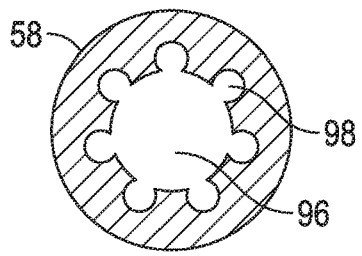
FIG. 4B illustrates a cross-sectional view of the magazine in FIG. 4A along cut lines 4B-4B, in accordance with at least one example.

FIG. 4A illustrates a side view of the magazine 56 and FIG. 4B illustrates a cross-sectional view of the magazine in FIG. 4A along cut lines 4B-4B, in accordance with at least one example. The magazine 56 can include a magazine head 60 and a magazine nose 58 extending from the magazine head 60. The magazine 56 can be cannulated and define a cannula 96 and a plurality of passageways 98.

Figure 7:
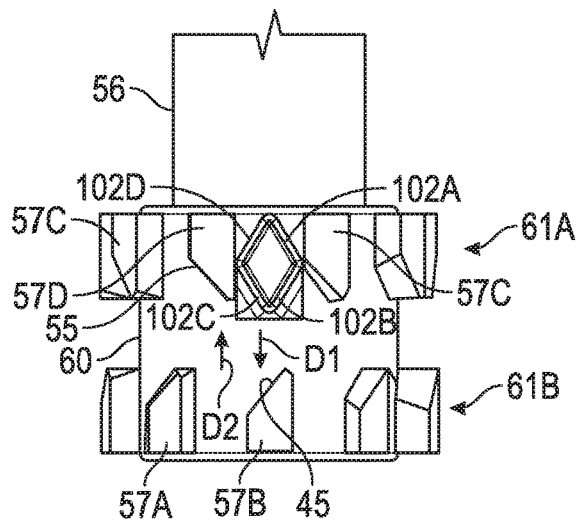
FIG. 7 illustrates a bottom view of a portion of the magazine engaged with a pawl head, in accordance with at least one example.

In an example, the magazine head 60 can include a plurality of fins 57. As discussed herein, the plurality of fins 57 can be configured to interact with an advancement pawl 86 (as shown in FIG. 7) to rotate the magazine 56 to align an adjacent passageway 98 with the projection of the piston. In an example, the plurality of fins 57 can be arranged in two rows along the magazine head 60. For example, the magazine head 60 can include a distal row of fins 61A and a proximal row of fins 61B. The fins 57 of the distal row of fins 61A can be radially offset from the fins 57 of the proximal row of fins 61B. The fins 57 can have an angled surface relative to a longitudinal axis of the magazine 56. For example, the fins 57 of the distal row of fins 61A can have a first angled surface 55 and the fins 57 of the proximal row of fins 61B can have a second angled surface 45.

Figure 5:
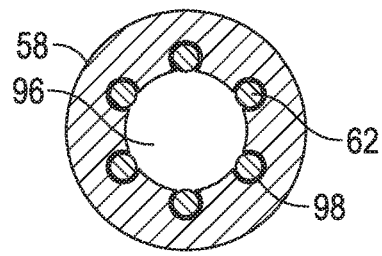
FIG. 5 illustrates a cross-sectional view of a magazine including a plurality of bone pins, in accordance with at least one example.

FIG. 5 illustrates a cross-sectional view of the magazine 56 including a plurality of bone pins 62, in accordance with at least one example. As discussed herein, the magazine .56 can define a cannula 96 and a plurality of passageways 98 that extend along a length of the magazine 56. The plurality of passageways 98 can be sized to receive a bone pin 62. Referring to FIGS. 3 and 5, when assembled, the shaft 68 of the piston 64 can be aligned with the cannula 96 of the magazine 56 and the projection 70 of the shaft 68 can be aligned with one of the plurality of passageways 98 of the magazine 56. When the trigger 18 is activated, the piston 64 can be forced down the barrel 24 such that the shaft 68 extends down the cannula 96 and the projection 70 engages with a bone pin 62 in the aligned passageway 98 and extends into the aligned passageway 98 to drive the bone pin 62 out from the magazine 56 and into fractured bone.

In an example, the plurality of passageways 98 of the magazine 56 are sized to limit each bone pin 62 to axial movement through the corresponding passageway 98, thereby stabilizing the bone pins 62 and ensuring that the desired length of the bone pins 62 is delivered along a straight path to avoid bending and/or breaking prior to the desired length being delivered from the bone pin gun 10. After use, the magazine 56 can be removed from the bone pin gun 10 and either refilled with new bone pins 62 or replaced.

In the example illustrated in FIG. 4A, 4B, and 5, the plurality of passageways 98 are circular. however, other shapes can be used. For example, the passageways 98 can have a circular shape, a triangular shape, a square shape, among others. Further, the passageways 98 can include more than one shape. However, the shape of the passageways 98 should substantially match the shape of the bone pin 62 to limit the bone pin to axial movement through the passageway 98.

Figure 6A:
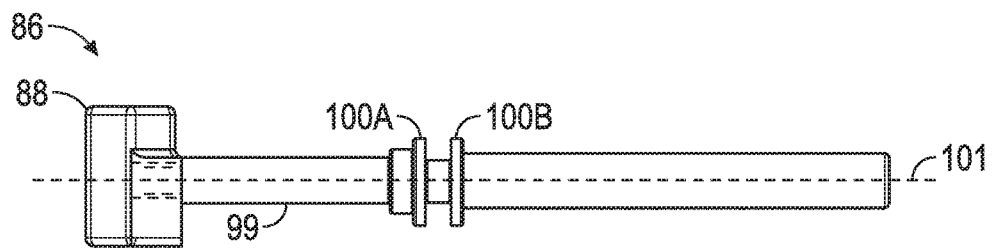
FIG. 6A illustrates a side-view of an advancement pawl, in accordance with at least one example.
Figure 6B:
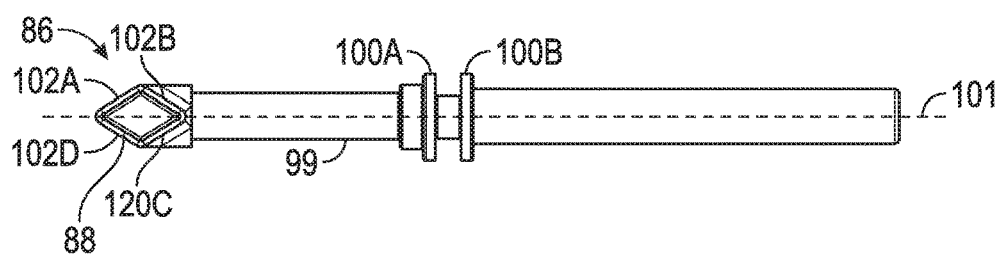
FIG. 6B illustrates a top view of the advancement pawl, in accordance with at least one example.

FIG. 6A illustrates a side view of the advancement pawl 86 and FIG. 6B illustrates a top view of the advancement pawl 86, in accordance with at least one example. The advancement pawl 86 can include a pawl shaft 99 and a pawl head 88. The pawl head 88 can be configured to engage with the plurality of fins 57 on the magazine head 60 to rotate the magazine 56 within the magazine holder 26 (as shown in FIG. 7). The pawl shaft 99 can include two rings 100A, 100B. The pawl head 88 can have a shape that cooperates with the angled surfaces 57, 45 of the plurality of fins 57 to rotate the magazine 56 within the magazine holder 26. As seen in FIG. 6B the pawl head 88 includes four angled surfaces 102A, 102B, 102C, and 102D. In some examples, only two angled surfaces can be provided, such as 102A and 102B.

Figure 8:
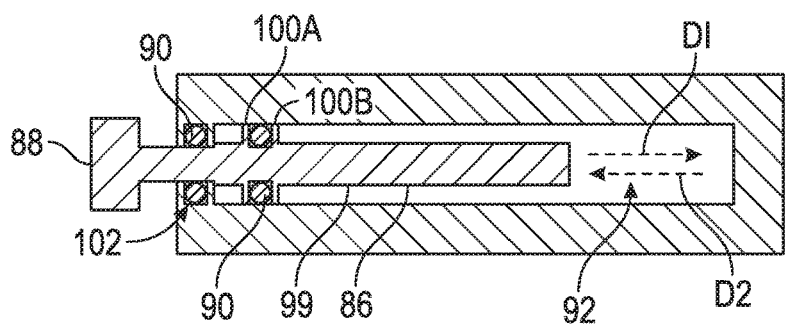
FIG. 8 illustrates a cross-sectional view of the advancement pawl, in accordance with at least one example.

FIG. 7 illustrates a bottom view of a portion of the magazine 56 engaged with the pawl head 88, in accordance with at least one example. FIG. 8 illustrates a cross-sectional view of the advancement pawl 86, in accordance with at least one example. The interaction between the advancement pawl 86 and the magazine 58 will be discussed with reference to FIGS. 7 and 8. The pawl head 88, as shown in FIG. 7, is at a raised position. At the biased position, the pawl head 88 can be positioned between two adjacent fins along the distal row of fins 61 A such as fins 57C and 57D. The advancement pawl 86 can be positioned within a bore 92 contained within the body portion 31. A portion of the pressurized gas can be configured to act on the advancement pawl 86 and force the advancement pawl 86 to move within the bore 92 in direction "D1." As the advancement pawl 86 moves in direction "D1," the pawl head 88 can move from the biased position between fin 57C and 57D to an intermediate position. For example, as the pawl head 88 is moving in direction "D1," surface 102B of the pawl head 88 can engage the angled surface 45 of a fin 57B along the proximal row of fins 61B. When the angled surface 102B engages angled surface 45, the magazine 58 can rotate relative to the advancement pawl 86 That is, the interaction between the two angled surfaces 102B and 45 rotates the magazine 56 and moves the pawl head 88 to the intermediate position located between two adjacent fins along the proximal row of fins 61B. For example, the pawl head 88 can move from the biased position, as illustrated in FIG. 7, along direction "D1," and to the intermediate position, for example, between fins 57B and 57A along the distal row of fins 57 61A.

A resilient member 90 having a first end and a second end can be provided. The resilient member 90 can be configured to return the pawl head 88 back to a biased position from the intermediate position. For example, the first end of the resilient member 90 can be coupled within a groove 102 of the body portion 31 and the second end of the resilient member 90 can be coupled to the advancement pawl 86 between the two rings 100A, 100B. The resilient member 90 as shown in FIG. 8 is in an uncompressed state. Once the trigger is activated, the pressurized gas can enter the bore 92 to force the advancement pawl 86 to the intermediate position. When the advancement pawl 86 is at the intermediate position, the resilient member 90 is in a compressed state. Once the pressurized gas exits the bore 92, the resilient member 90 can be configured to transition from the compressed state, when the pawl head 88 is at the intermediate position, to the uncompressed state. When the pawl head 88 is the biased position.

As the resilient member 90 transitions from the compressed state to the uncompressed state, the advancement pawl 86 moves along direction "D2." For example, the pawl head 88 can move from between fin 57A and 57B (the intermediate position), along direction "D2" and toward fin 57D. As the pawl head 88 moves toward fin 57D, the pawl head 88 will contact fin 57D such that angled surface 102A can engage the angled surface 55 of fin 57D. As the angled surface 55 of fin 57D interacts with the angled surface 102A of the pawl head 88, the magazine 56 will slide along angled surface 55 of fin 57D and rotate relative to the pawl head 88. The pawl head 88 will continue to move in direction "D2" until stopping at the biased position, for example, between two adjacent fins 57 along the distal row of fins 61A. In the example illustrated in FIG. 7, the pawl head 88 would move from between fins 57A and 57B to between fins 57D and 57E, as angled surface 102A of the pawl head 88 interacts with angled surface 55 of fin 57D.

While FIG. 7 illustrates the magazine head 60 including a plurality of fins 57, other designs of the magazine head 60 can be utilized for the automatic bone pin advancement. In an example, the magazine head 60 could include a number of straight and helical grooves. In an example, the number of straight grooves can equal the number of passageways of the magazine. The straight lines are configured to be in line with a respective passageway of the plurality of passageways of the magazine. The helical grooves can run between the straight grooves, from end to end. The helical groove can also have strategic ramps and steps built into them. An advancement pawl could be used and travel along the helical grooves to rotate the magazine.

Figure 9:
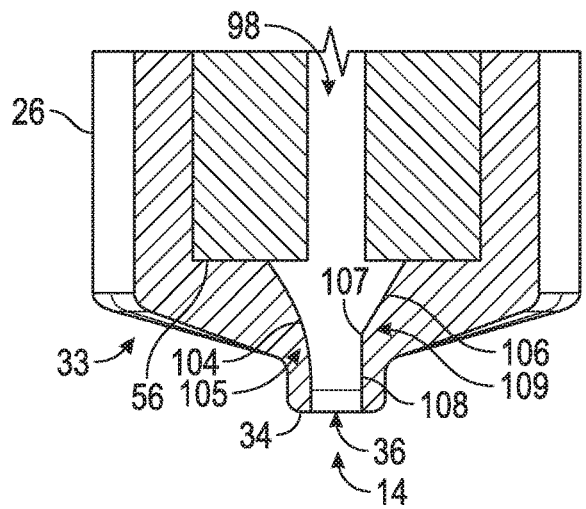
FIG. 9 illustrates a cross-sectional view of a portion of the magazine holder and the magazine, in accordance with at least one example.

FIG. 9 illustrates a cross-sectional view of a portion of the magazine holder 26 and the magazine 56, in accordance with at least one example. The trimming end 33 can be located at a distal end of the magazine holder 26 and includes a bone contacting surface 34 and the trimming bore 36. As seen in FIG. 9, a passageway 98 of the magazine 56 is aligned with the trimming bore 36. The trimming bore 36 can be defined by a breaking edge 105 having a curved surface 104 and a relief edge 109 having a chamfered surface including two straight surfaces 106, 108 forming an edge 107.

Referencing FIGS. 3, 7, and 9, the trimming operation relies on both the unique geometry of the trimming bore 36 and the actuation of the advancement pawl 86. The geometry of the trimming bore 36 combined with the actuation of the advancement pawl 86 can result in a single break in the bone pin 62 after the bone pin 62 is implanted into fractured bone. As the advancement pawl 86 pulls back and places the pawl head 88 into the intermediate position between fins 57A and 57B, the magazine 56 can be partially rotated and the bone pin 62 can be placed in tension. However, it isn't until the pawl head 88 transitions from the intermediate position to the baised position between fins 57D and 57E before the bone pin 62 is trimmed (e.g., with a single break) and a subsequent passageways 98 is aligned with the trimming bore 36.

FIG. 10 illustrates a top view of a portion of the barrel 24 and the mode selector ring 32, in accordance with at least one example. The mode selector ring 32 can be rotatable about the barrel 24 and configured to switch between mode positions. As shown in FIG. 10, the mode selector ring 32 can include an assemble mode position 118 for an assemble mode, a depth mode position 118 for a depth mode, and a ready mode position 120 for a ready mode. The barrel can include the markings "assemble," "depth," and "ready" to indicate and label each mode position. Further, the barrel 24 can include indicator marker 114 and have the marking "select," which indicates which mode the bone pin gun is currently operating, To switch between modes a user can apply a rotational force to the mode selector ring 32 to rotate the mode selector ring 32 such that the desired mode is aligned with the indicator 114.

As discussed herein, the various modes work together to increase the safety and usability of the bone pin gun. In an example, when the bone pin gun is at the assemble mode position 118, the magazine holder 26 and the collar 22 can be releasably coupled to the body portion 31. For example, once all the bone pins have been discharged from the magazine, to refill or replace the magazine, a user would put the turn the mode selector ring 32 to the assemble mode position 118. Once the bone pin gun is in the assemble mode, the user would be able to disengage the magazine and collar from the body portion. However, as discussed herein, the magazine holder 26 and the collar 22 are only allowed to become uncoupled from the body portion when the mode selector ring 32 is at the assemble mode position 118.

In an example, when the mode selector ring 32 is at the ready mode position 120, the trigger of the bone pin gun is able to be activated (e.g., by pulling with finger). For example, when the surgeon wishes to discharge a bone pin, they can rotate the mode selector ring 32 to the ready mode position 120 and activate the trigger. However, as discussed herein, the trigger 18 is only allowed to be activated when the mode selector ring 32 is at the ready mode position 120.

Figures 11, 12:
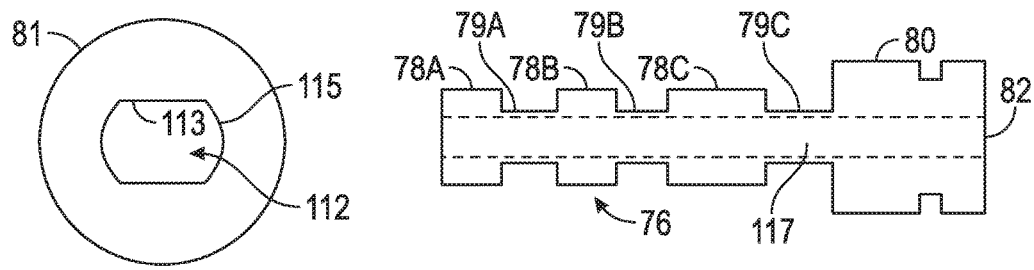
FIG. 11 illustrates a depth lock, in accordance with at least one example.
FIG. 12 illustrates a hard stop, in accordance with at least one example.

As shown in FIG. 10, the barrel 24 includes the depth selector ring 30. In an example, when the bone pin gun is at the depth mode position 116, the depth selector ring 30 can be configured to move along a length of the barrel 24 to adjust a length of a bone pin that discharged from the bone pin gun and into the bone fragment. The depth selector ring 30 can include a window 110. The widow 110 can indicate to a user what length of the bone pin will be discharged from the bone pin gun. In an example, the barrel 24 can include depth markings 112 to indicate the various lengths. As shown in FIG. 10, the barrel 24 includes depth markings 112 "25," "38", and "50" indicating 25 millimeters (mm), 38 mm, and 50 mm. The window 110 is encircling depth marking 112 "25" indicating to the surgeon that 25 mm of the bone pin will be implanted into the bone fracture. As discussed herein, the depth selector ring 30 can be coupled to a hard stop 74 positioned within the body portion 31 (as shown in FIGS. 3 and 12) via rods 35. The hard stop 74 can interact with a depth lock 81 positioned within the body portion 31 (as shown in FIGS. 3 and 11) to move the depth selector ring 30 along the barrel. However, as discussed herein, the depth selector ring 30 is only allowed to move along the barrel 24 when the mode selector ring 32 is at the depth mode position 116.

Each mode position 118, 116, 120 can enables the bone pin gun to perform a particular function. However, the function of each mode is only functional when the mode selector ring 32 is at the mode position that corresponds to that particular function. In an example, When the mode selector ring 32 is at the ready mode position 120, the magazine holder and collar are locked to the body portion and the depth selector ring 30 is locked in position and unable to move along the barrel 24. "Locked to the body portion" is used herein to refer to the collar 22 and the magazine holder 26 not being able to be disengaged from the body portion 31 without incurring structural damage. Further, "locked in position" is used herein to refer to the depth selector ring 30 not being able to be moved along the barrel 24 without incurring structural damage.

In an example, when the mode selector ring 32 is at the assemble mode position 118, the trigger is locked at the initial position and unable to be activated and the depth selector ring 30 is locked in position and unable to move along the barrel 24. "Unable to be activated" is used herein to refer to the trigger 18 not being able to be activated (e.g., pressed down) without incurring structural damage. When the mode selector ring 32 is at the ready mode position 120, the magazine holder and magazine are locked to the body portion and the depth selector ring 30 is locked in position along the barrel 24.

FIG. 11 illustrates the depth lock 81, in accordance with at least one example. The depth lock 81 can be positioned within the body portion 31 of the bone pin gun 10 toward a distal end of the barrel 24, as shown in FIG. 3. The depth lock 81 can include an opening 112 that can interact with the hard stop 74 (as shown in FIG. 12). The opening 112 can be defined by two substantially flat parallel surfaces 113 and two curved surfaces 115.

FIG. 12 illustrates a side view of the hard stop 74, in accordance with at least one example. The hard stop 74 can include a head portion 80 having a stopping surface 82 and an adjustment portion 76 extending from the head portion 80. The location of the hard stop 74 inside the barrel can determine where the piston head will stop. Therefore, changing the location of the hard stop 74 can change the depth to which the bone pins are driven.

The hard stop 74 can define a cannula 117 that is configured to receive at least a portion of the piston 64 and the resilient member 72 (as shown in FIG. 3). The adjustment portion 76 includes two opposing rows including plurality of shoulders 78A, 78B, and 78C (herein referred to collectively as "shoulders") and a plurality of grooves 79A, 79B, and 79C (herein referred t© collectively as "grooves 79"). In an example, between the two rows of the shoulders 79 and grooves 79, the adjustment portion 76 can include two opposing flat surfaces 119 (as shown in FIG. 13). The head portion 80 can be coupled to the mode selector ring 32 (shown in FIG. 3) and to the depth selector ring 30 via the rods 35 (see FIGS. 3 and 10).

FIG. 13 illustrates an assembled view of the depth lock 81 and the hard stop 74, in accordance with at least one example. The hard stop 74 and depth lock 81 behave like a lock and key. The opening 112 can receive a portion of the adjustment portion 76. The cross-sectional shape of the adjustment portion 76, along the shoulders 78, is such that when the shoulders 78 are positioned adjacent to the curved surfaces 115 of the opening 112 and the flat surfaces 119 are positioned adjacent to the flat surfaces 113 of the opening 112, the hard stop 71 is in an unlocked position and is able to move relative to the depth lock 81. The head portion 80 of the hard stop 74 can be coupled to the mode selector ring 32 and also coupled to depth selector ring 30 via the rods 35, as seen in FIGS. 3 and 10. As discussed here, the hard stop 74 is coupled to the mode selector ring 32 such that when the mode selector ring 32 is rotated from the depth mode position, the rotation of the mode selector ring 32 turns the hard stop 74 approximately 180 degrees. Once the mode selector ring 32 is rotation, the cross-sectional shape of the hard stop 74 can no longer fit through the opening 113 and the hard stop 74 is locked in place relative to the depth lock 81.

Referring to FIG. 3, by moving the depth selector ring 30 along the barrel 24, the stopping surface 82 of the hard stop 74 can change positions within the barrel 24. When the bone pin gun 10 is fired, the piston 64 can be forced down the barrel 24 and stops when the head 66 of the piston 64 contacts the stopping surface 82. Thus, the closer the stopping surface 82 of the hard stop 74 is positioned to the proximal end 12 of the bone pin gun 10, the shorter the distance the projection 70 on the piston 64 can extend into the passageway 98 and the amount of the bone pin 62 discharged from the bone pin gun 10 is shortened. Similarly, as the position of the stopping surface 82 of the harstop 76 moves toward a distal end of the barrel 24, the greater the length of the bone pin 62 that will be discharged from the bone pin gun 10.

When the mode selector ring 32 is at the depth position mode 116 (as shown in FIG. 10), the hard stop 74 can be rotated to the unlocked position, as seen in FIG. 13, such that the adjustment portion 76 can pass through the opening 112 of the depth lock 81. When the hard stop 74 is at the unlocked position, the depth selector ring 30 can be moved along the barrel 24 to move the hard stop 74 relative to the depth lock 81. Once the desired length is achieved, the mode selector ring 32 can be switched to a different mode position, thereby turning the hard stop 74 approximately 180 degrees and locking the hard stop 74 to the depth lock 81. For example, if the hard stop 74 in FIG. 13 were rotated 180 degrees, the groove 79C would extend across the opening 112 and the shoulder 79C would extend beyond the opening 112 thereby preventing the hard stop 74 from moving relative to the depth lock 81.

In the example shown in FIG. 13, when groove 79C extends across the opening 112 of the depth lock 81, the depth selector ring 30 would be indicating "50" (in FIG. 10), when groove 79B extends across the opening 112 of the depth lock 81, the depth selector ring 30 would be indicating "38" (in FIG. 10), and when groove 79A extends across the opening 112 of the depth lock 81, the depth selector ring 30 would be indicating "25" (in FIG. 10).

While the example illustrated in FIG. 10 includes three different depths, the number of the available depths can vary. For example, the number of depths available will correspond to how many locking positions there are along the adjustment portion 76 of the hard stop 74. Further, the distance between each depth marker 112 will correspond to the thickness of each shoulder of the hard stop 74.

FIG. 14 illustrates a cross-sectional view of a portion of the barrel 24 and a portion of the magazine holder 26, in accordance with at least one example. For simplicity, the collar is not shown in FIG. 14. As shown in FIG. 14, the engaging end 40 of the magazine holder 26 is disengaged from the engaging end 52 of the barrel 24 and the mode selector ring 32 is at the assemble mode position 118 (as shown in FIG. 10).

A first locking cam 128 and a second lock cam 126 can be positioned within the barrel 24. In an example, the first and second locking cams 128, 126 are connected and spring loaded. The mode selector ring 32 can include an opening 124. When the mode selector ring 32 is at the assemble mode position, the engaging end 40 of the magazine holder 26 can disengage from the engaging end 52 of the barrel 24 releasing the first locking cam 128 from a compressed state. The first locking cam 128 can transition to an uncompressed state, as illustrated in FIG. 14. That is, the first locking cam 128 is biased to the position illustrated in FIG. 14. Similarly, the second locking cam 126 is in an uncompressed state and biased to the position illustrated in FIG. 14.

In the uncompressed state, the second locking cam 126 extends upward into the opening 124 of the mode selector ring 32 thereby preventing the mode sector ring 32 from rotating to switch between modes. Thus, when the magazine holder 26 is not coupled to the body portion 31, the bone pin gun 10 is unable to be fired and the depth of the bone pins is unable to be changed.

When the magazine holder 26 is coupled to the body portion, the first locking cam 128 can transition into the compressed state. Since the first locking cam 126 is coupled to the second locking cam 128, as the first locking cam 126 moves from the uncompressed state to the compressed state, the second locking cam 128 also moves to a compressed state. In the compressed state, the second locking cam 128 is positioned such that the second locking cam 128 does not interfere with the rotation of the mode selector ring 32. In other words, the second locking cam 128 is positioned beneath the opening 124 such that the opening 124 is free from the second locking cam 128 and the mode selector ring 32 is free to rotate about the barrel 24.

FIG. 15 illustrates a partial perspective view of the trigger assembly 13 and the mode selector ring 32, in accordance with at least one example. In an example, the mode selector ring 32 can include a groove 130 extending along a length of the mode selector ring 32, In an example, the trigger assembly 13 includes the trigger 18. The trigger 18 can include a locking portion 131 extending along a surface of the barrel 24 and a projection 131 extending from the locking portion 131. The mode selector ring 32, as shown in FIG. 15, is not in the ready mode position 120. Since the mode selector ring 32 is not in the ready mode position 123, the trigger 18 can be prevented from being activated. That is, the trigger 18 cannot be pulled to move the trigger from the initial position to fire the bone pin gun. As seen in FIG. 15, the trigger 18 can be locked (e.g., prohibited from being pulled) because the projection is abutting a portion of the mode selector ring 32. Once the mode selector ring 32 is at the ready mode position 120 (as shown in FIG. 10), the groove 130 can be configured to align with the projection 133 such that the projection 133 will travel along the path of the groove 130 when the trigger 18 is pulled to fire the bone pin gun 10.

FIG. 16 illustrates a cross-sectional view of the gas valve assembly 69, as shown in FIG. 3. As discussed herein, gas canister can be positioned within a bore of the gas housing 20 and a screw cap can be removably coupled to the gas housing 20, for removing and replacing the gas canister. As the screw cap is screwed in, the gas canister can advance toward the gas valve assembly 69. As shown in FIG. 16, the gas valve assembly 69 can be positioned within the gas housing 20 can include a puncture needle 134, a chamber 146, a body portion 142, and a resilient member 136. As the screw cap is screwed into the gas housing 20, the gas canister can be forced toward the puncture needle 134 such that the puncture needle 124 punctures the gas canister. Once the gas canister is punctured, the pressurized gas can exit the gas canister and can follow gas path 141 through the puncture needle 134, into the chamber 146, through the outlet 147, and into the first gas channel 65. As the pressurized gas enters the chamber 146, the pressurized gas can force the body portion 142 to move within the chamber 146 and expose the outlet 147. When the pressurized gas enters the chamber 146 and pushes on the body portion 142, the resilient member 136 can be configured to transition from an uncompressed state to a compressed state. As seen in FIG. 16, the resilient member 136 is in the compressed state and the outlet 147 is exposed. Once the pressurized gas depletes and there is no more pressurized gas entering the chamber 146, the resilient member 136 can transition from the compressed state to the uncompressed state such that the body portion 142 covers the gas outlet 147 sealing the first gas channel from the exterior.

FIG. 17 illustrates a cross-sectional view of the filter valve assembly 67, in accordance with at least one example. The filter valve assembly 67 can include a ball dent 149, a body portion 148, and a resilient member 152. As seen in FIG. 17, the resilient member 152 can be configured to be at an uncompressed state such that the ball dent 149 is positioned in an outlet 153 of the gas exit channel 151, thereby sealing the gas exit channel 151 to the exterior. As the pressurized gas leaves the bone pin gun 10 via the gas exit channel 151, the pressurized gas pushes on the ball dent transitioning the resilient member 152 from the uncompressed state to a compressed state. When the resilient member 152 is in the compressed state, the ball dent 149 can move such that the ball dent 149 is no longer sealing the outlet 153 and the pressurized gas can pass through the filter valve assembly 67 via gas outlet 150, through a filter, and to the exterior of the bone pin gun 10.

Referring back to FIG. 3, the body portion 31 can define a first gas channel 65 that connects a gas canister (not shown) to a regulator 71 and a second gas channel 73 that connects the regulator 71 to the valve assembly 63. In operation, pressurized gas can flow from the gas canister to the regulator via the first gas channel 65 and from the regulator 71 to the valve assembly 63 via the second gas channel 73.

Gas canister 42 contains a supply of pressurized gas. In an example, the gas canister 144 can contain pressurized carbon dioxide gas ($CO_2$) or nitrogen gas ($N_2$). Advantageously, the gas canisters can be inexpensive, are readily commercially available, and are able to power the bone pin gun 10 independently without any other secondary power source, such as a battery. Pressurized gas is generally commercially available in 12-gram supplies, although the bone pin gun 10 can be designed to accommodate gas canisters 42 of various types and sizes. The pressure inside the gas canister 42 can be as low as approximately 300 pound per square inch (psi) (approximately 21 kilograms per square centimeter; $kg/cm^2$), 400 psi (28 $kg/cm^2$), 500 psi (35 $kg/cm^2$), or 600 psi (42 $kg/cm^2$), and as high as approximately 700 psi (49 $kg/cm^2$), 800 psi (56 $kg/cm^2$), 900 psi (63 $kg/cm^2$), 1000 psi (70 $kg/cm^2$), or more, although the pressure inside the gas canister 42 can vary with temperature. When each new gas canister is inserted into the gas housing 20, the gas valve assembly 69 can puncture the gas canister 42 to initiate airflow from the gas canister 42 to the regulator 71 via the first gas channel 65.

The regulator 71 can be provided to control the pressure of the gas that is delivered to valve assembly 63. When the pressure in a valve body 84 of the valve assembly 63 reaches a desired threshold, regulator 71 cuts off the continued flow of pressurized gas to valve body 63. Therefore, even if the pressure in the gas canister 42 fluctuates, the regulator 71 is able to deliver the pressurized gas to valve body 63 at a substantially constant pressure.

The valve assembly 63 can be positioned at the proximal end 12 of the barrel 24. The valve assembly 63 can include the valve body 84, the valve return spring 87, and the plug 85. The valve body 84 can be a hollow component that defines gas chamber 81. Gas chamber 89 of valve body 84 can include an inlet that communicates with second gas channel 73 to receive the pressurized gas exiting the regulator 71. Gas chamber 89 of valve body 84 can also include a sealed outlet that communicates with the piston 64 to deliver pressurized gas from gas supply assembly 140 to the piston 64.

Plug 85 of valve assembly 120 is sized for receipt within the outlet of valve body 84, The plug 85 can translate axially relative to valve body 84 to close and open valve assembly 85. Valve assembly 85 can close when plug 85 seals outlet of valve body 84 closed, thereby preventing airflow from the gas chamber 89. Valve assembly 63 opens when the tapered end 91 of the plug 85 translates into the outlet of valve body 84 and opens the outlet, thereby allowing pressurized gas to escape from gas chamber 89 of valve body 63.

As discussed herein, various components of the bone pin gun can be disposable. For example, the magazine holder, magazine, gas canister, and filter. For example, the filter can be switched between patients or when it becomes clogged, the gas canister can become empty, and all the bone pins included within a magazine can be delivered and needs replacement.

The alignment of the bone pin relative to a patient's anatomy can be important. With handheld delivery tools, alignment is completely dependent on the surgeon. A slight flinch, twist, or misjudgment in a single direction can be extremely hazardous, even life-threatening. In order to more easily locate, align, and deploy bone pins, a custom nosepiece can be developed that has two distinct ends. A distal end that allows accurate placement on patient specific locations and a proximal end that attaches to the bone pin gun. The distal end can include a patient specific surface, where the patient specific surface defines a negative impression of a portion of a treatment surface (e.g., a bone surface) of a patient.

In an example, the nose piece could be configured to be placed on the distal end of the magazine holder. In another example, the nosepiece can replace the magazine holder and be configured to receive the magazine and perform the functions of the magazine holder, as described herein. The nosepieces can be produced in a number of ways. For example, either from direct impression molding or from imaging based techniques (CT scan). The procedure would comprise two visits. During the first visit, the physician would take necessary impressions/images/measurements for accurate location of a desired bone pin. These would be sent out for processing during which the nosepiece would be formed, the magazine would be inserted into the nose and the bone pin could be delivered to the patient via the patient specific nose.

The bone pins are configured to be driven into bone fragments to secure the bone fragments together. Bone pins (such as bone pins 62) can be constructed of a biocompatible polymer including thermosets, plastics, elastomers, semi-crystalline polymers, and amorphous polymers, among others. In an example, the biocompatible polymer can be biodegradable. For example, the bone pins can be constructed of a biodegradable polymer, such as polylactide (PIA). Further, the bone pins can be formed of polystyrene, poly methyl methacrylate, polycarbonate, or a fiber-reinforced polymer, for example, It also is within the scope of the present disclosure that the bone pins can be constructed of a biocompatible, non-ferrous metal, such as magnesium. In an example, the bone pins can be formulated with radiopacifiers, antibiotics, and therapeutic agents.

The bone pins can be a smooth cylinder or other contoured geometry of any length, diameter, and/or cross-section. Further, the bone pins can include static and/or deployable fixation features such as ribs, barbs, or sutures, The ends of the bone pins can have various shapes. In one example, the ends of bone pin can have flat surface. However, other geometries can be utilizes such as a pointed or angled end.

As discussed herein, the magazine can house multiple bone pins. As discussed herein, the projection of the piston is received within a passageway of the magazine to drive a bone pin from the magazine. In that instance, the bone pins are delivered in a singular, sequentially independent fashion. However, other examples are contemplated. In an example, the piston can include more than one projection that is configured to be received within more than one passageway when the piston is fired. In that instance, two or more bone implants are discharged from the bone pin gun simultaneously. The bone implants discharged can be adjacent to each other, diametrically opposed, or another configuration. The plurality of the fins of the magazine can also be adjusted to accommodate discharging more than one bone pin. For example, the thickness of the fins can be adjusted such that one the bone pin has fired, the magazine rotates such that passageways containing bone pins are aligned with the two or more projections contained on the piston shaft. In another example, the piston can include a single projection but more than one hone pins can be discharged from the gun. For example, more than one bone pins can be coupled together such that as the single projection is received within a passageway containing a hone pin to drive the hone pin from the magazine, any other bone pins coupled to the bone pin interacting with the projection will be driven form the magazine. Thus, more than one hone pin can be deployed at a time in a grouped deployment configuration.

The present application also provides a method 200 for forming a magazine including a plurality of bone pins. In an example, the bone pins can be injected molded into the magazine. For example, bone pins 62 can being injected molded into magazine 56. The method 200 can include a plastic-on-plastic injection molding process. At step 202, the method 200 can include forming a magazine having a plurality of passageways and a cannula, where the magazine is formed from a first material. For example, method 200 can include forming the magazine 56 including a plurality of passageways 98 and a cannula 96, as discussed herein. In an example, the plurality of passageways 98 and the cannula 96 can extend along the length of the magazine, The number, shape, and size of the plurality of passageways 98 can vary depending on the application. In an example, the diameter of the passageways can be within a range of from about 0.5 millimeters (mm) to about 3 mm, such as 1 mm and 2 mm.

At step 204, the method 200 can include injection molding the bone pins into the magazine, where the bone pins are formed of a second material. In an example, the first and second materials are both polymers; however, the first material and second material have differing thermal properties. For example, the first material of the magazine has higher thermal properties than the second material of the bone pins so that the magazine does not deform during the injection molding of the bone pins. In an example, there is a predefined threshold difference between the first material and the second material for at least one of a deformation temperature, a glass transition temperature, and melt temperature. Maximizing the difference between the thermal properties of the first and second material can minimize risks of damaging the parts during the process, such as deforming the magazine during the injection molding of the bone pins. The produced product including the magazine having the injection molded implants can be utilized in the bone pin gun such as bone pin gun 10, as described herein.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a tool, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the disclosure should be determined with reference to the appended claims, along with the full scope of equivalents to which such claims are entitled.

What is claimed is:

1. A tool for stabilizing a fractured bone, comprising:
   a body portion including a barrel, a handle, and a mode selector ring, the mode selector ring rotatable about the barrel and configured to switch between a ready mode position and an assemble mode position;
   a magazine having a magazine head, a magazine nose extending from the magazine head, and a plurality of passageways, wherein one or more passageways of the plurality of passageways is configured to receive a bone pin;
   a magazine holder configured to receive the magazine;
   a collar defining an opening configured to receive a portion of the magazine holder;
   a piston having a head, a shaft extending from the head, and a projection coupled to the shaft, the projection configured to be received within a first passageway of the plurality of passageways; and
   a trigger coupled to the body portion, wherein, when the trigger is activated, the piston is configured to apply sufficient force to the bone pin to drive the bone pin axially from the first passageway.

2. The tool of claim 1, wherein, when the mode selector ring is at the assemble mode position, the magazine holder is configured to be releasably coupled to the body portion and when the mode selector ring is at the ready mode position, the trigger is configured to be activated.

3. The tool of claim 1, wherein, when the mode selector ring is at the ready mode position, the magazine holder is locked to the body portion.

4. The tool of claim 1, wherein, when the mode selector ring is at the assemble mode position, the trigger is locked at an initial position.

5. The tool of claim 1, wherein the mode selector ring further includes:
   a depth mode position such that the mode selector ring is rotatable about the barrel to switch between the depth mode position, the ready mode position, and the assemble mode position.

6. The tool of claim 5, further including:
   a depth selector positioned along the barrel, wherein, when the mode selector ring is at the depth mode position, the depth selector is configured to move along a length of the barrel to adjust a length of the bone pin that is driven axially from the first passageway.

7. The tool of claim 6, wherein, when the mode selector ring is at the depth mode position, the trigger is locked at an initial position and the magazine holder is locked to the body portion, wherein, when the mode selector ring is at the ready mode position, the depth selector is locked in position along the barrel and the magazine holder is locked to the body portion, and wherein, when the mode selector ring is at the assemble mode position, the depth selector is locked in position along the barrel and the trigger is locked at the initial position.

8. The tool of claim 1, further including:
   a pressurized gas source for supplying a pneumatic force to the head of the piston to axially translate the piston relative to at least the body portion and the magazine.

9. A tool for stabilizing a fractured bone, comprising:
   a body portion including a barrel, a handle, and a mode selector ring, the mode selector ring rotatable about the barrel and configured to switch between a ready mode position and an assemble mode position;
   a magazine having a magazine head, a magazine nose extending from the magazine head, and a plurality of passageways, wherein one or more passageways of the plurality of passageways is configured to receive a bone pin;
   a magazine holder configured to receive the magazine;
   a collar defining an opening configured to receive a portion of the magazine holder;
   a piston having a head, a shaft extending from the head, and a projection coupled to the shaft, the projection configured to apply sufficient force to the bone pin, when present within a first passageway of the plurality of passageways, to drive the bone pin from the first passageway;
   an advancement pawl disposed within the body portion, the advancement pawl including a pawl shaft and a pawl head, wherein the pawl head is configured to interact with the magazine head to rotate the magazine and align a second passageway of the plurality of passageways with the projection.

10. The tool of claim 9, wherein the magazine head includes a plurality of fins, each fin of the plurality of fins having an angled surface relative to a longitudinal axis of the magazine, wherein the angled surface is configured to interact with the pawl head to rotate the magazine.

11. The tool of claim 10, wherein a first portion of the plurality of fins are arranged in a proximal row of fins circumferentially spaced around the magazine head and a second portion of the plurality of fins are arranged in a distal row of fins circumferentially spaced around the magazine head, the first portion of the plurality of fins circumferentially offset from the second portion of plurality of fins.

12. The tool of claim 10, wherein the pawl head has a shape including at least two angled surfaces relative to a longitudinal axis of the advancement pawl, the at least two angled surfaces of the pawl head configured to engage with one or more angled surfaces of the plurality of fins to rotate the magazine.

13. The tool of claim 9, further including:
   a trigger coupled to the body portion, wherein, when the trigger is activated, the piston is configured to drive the first bone pin axially from the first passageway.

14. The tool of claim 9, wherein the trigger has an initial position, an end position, and an intermediate position located between the initial position and end position, wherein, upon activation of the trigger from the initial position to the intermediate position, the piston is configured to drive the bone pin axially from the first passageway, and upon activation of the trigger from the intermediate position to the end position, the pawl head is configured to interact with the magazine head to rotate the magazine and align the second passageway with the projection.

15. The tool of claim 9, wherein the magazine holder includes a trimming end defining a trimming bore that is configured to align with the projection of the piston and trim the bone pin when the magazine rotates within the magazine holder.

16. The tool of claim 15, wherein the trimming bore includes a breaking edge including a curved surface and a relief edge having a chamfered surface including two straight surfaces forming an edge.

17. The tool of claim 9, further including:
a pressurized gas source for supplying a pneumatic force to the head of the piston to axially translate the piston relative to body portion and the magazine.

18. A system for bone fixation, comprising:
a body portion including a barrel, a handle, and a mode selector ring, the mode selector ring rotatable about the barrel and configured to switch between a ready mode position and an assemble mode position;
a magazine including a plurality of passageways, wherein one or more passageways of the plurality of passageways is configured to receive a bone pin;
a magazine holder configured to receive the magazine;
a collar defining an opening configured to receive a portion of the magazine holder; and
a piston having a head, a shaft extending from the head, and a projection coupled to the shaft, the projection sized for receipt within a first passageway of the plurality of passageways, the projection configured to apply sufficient force to the bone pin when present within the first passageway, to drive the bone pin axially from the first passageway.

19. The system of claim 18, further including at least one of:
a plurality of magazines, wherein each magazine include at least one bone pin positioned in a first passageway of the plurality of passageways; and
one or more gas canisters for supplying a pneumatic force to the head of the piston to axially translate the piston relative to at least the body portion and the magazine.

20. The system of claim 18, further including:
a trigger coupled to the body portion, wherein, when the trigger is activated, the piston is configured to drive the first bone pin axially from the first passageway; and
an advancement pawl disposed within the body portion, the advancement pawl including a pawl shaft and a pawl head, wherein the pawl head is configured to interact with a magazine head to rotate the magazine and align a second passageway of the plurality of passageways with the projection.

* * * * *